(12) United States Patent
Singh

(10) Patent No.: US 9,993,454 B2
(45) Date of Patent: Jun. 12, 2018

(54) SOLID NANOPARTICLE FORMULATION OF WATER INSOLUBLE PHARMACEUTICAL SUBSTANCES WITH REDUCED OSTWALD RIPENING

(71) Applicant: Luminus Biosciences, Inc., San Antonio, TX (US)

(72) Inventor: Chandra Ulagaraj Singh, San Antonio, TX (US)

(73) Assignee: Luminus Biosciences, Inc., San Antonio, TX (US)

( * ) Notice: Subject to any disclaimer, the term of this patent is extended or adjusted under 35 U.S.C. 154(b) by 0 days. days.

(21) Appl. No.: 14/278,947

(22) Filed: May 15, 2014

(65) Prior Publication Data
US 2016/0367514 A1 Dec. 22, 2016

Related U.S. Application Data

(63) Continuation of application No. 12/309,581, filed as application No. PCT/US2007/016599 on Jul. 24, 2007, now Pat. No. 8,728,527.
(Continued)

(51) Int. Cl.
A61K 9/10 (2006.01)
A61K 31/337 (2006.01)
A61K 9/51 (2006.01)
A61K 31/427 (2006.01)
A61K 31/341 (2006.01)
A61K 31/381 (2006.01)
A61K 9/16 (2006.01)

(52) U.S. Cl.
CPC .............. *A61K 31/337* (2013.01); *A61K 9/10* (2013.01); *A61K 9/1617* (2013.01); *A61K 9/1658* (2013.01); *A61K 9/1682* (2013.01); *A61K 9/5123* (2013.01); *A61K 9/5169* (2013.01);
(Continued)

(58) Field of Classification Search
None
See application file for complete search history.

(56) References Cited

U.S. PATENT DOCUMENTS 4,348,385 A 9/1982 Synek
4,610,868 A 9/1986 Fountain et al.
(Continued)

FOREIGN PATENT DOCUMENTS

WO 1998/00110 A1 1/1998
WO 1998/14174 A1 4/1998
(Continued)

OTHER PUBLICATIONS

Lindsfor et al. (Amorphous Drug Nanosuspensions. 1. Inhibition of Ostwald Ripening, Langmuir 2006, 22, 906-910, Final Form Nov. 1, 2005).*
(Continued)

*Primary Examiner* — Robert A Wax
*Assistant Examiner* — Melissa S Mercier
(74) *Attorney, Agent, or Firm* — Nevrivy Patent Law Group P.L.L.C.

(57) ABSTRACT

The present invention belongs to the fields of pharmacology, medicine and medicinal chemistry. The present invention provides novel pharmaceutical compositions composed of solid nanoparticles dispersed in aqueous medium of substantially water insoluble pharmaceutical substances such as docetaxel with reduced Ostwald ripening.

12 Claims, 25 Drawing Sheets

Chemical Structure of Taxanes

Related U.S. Application Data

(60) Provisional application No. 60/832,587, filed on Jul. 24, 2006.

(52) U.S. Cl.
CPC .......... *A61K 31/341* (2013.01); *A61K 31/381* (2013.01); *A61K 31/427* (2013.01)

(56) References Cited

U.S. PATENT DOCUMENTS

| | | | |
|---|---|---|---|
| 4,814,470 | A | 3/1989 | Colin et al. |
| 4,826,689 | A | 5/1989 | Violanto et al. |
| 4,997,454 | A | 3/1991 | Violante et al. |
| 5,100,591 | A | 3/1992 | Leclef et al. |
| 5,439,686 | A | 8/1995 | Desai et al. |
| 5,560,933 | A | 10/1996 | Soon-Shiong et al. |
| 5,916,596 | A * | 6/1999 | Desai .................. A61K 9/0019 424/439 |
| 6,074,986 | A | 6/2000 | Mulqueen et al. |
| 6,106,855 | A | 8/2000 | Haynes et al. |
| 6,207,178 | B1 | 3/2001 | Westesen et al. |
| 6,348,215 | B1 | 2/2002 | Straubinger et al. |
| 6,610,321 | B2 | 8/2003 | Huang et al. |
| 6,616,917 | B2 | 9/2003 | Lorant et al. |
| 6,749,868 | B1 | 6/2004 | Desai et al. |
| 8,728,527 | B2 | 5/2014 | Singh |
| 2004/0247660 | A1 | 12/2004 | Singh |
| 2005/0009908 | A1 | 1/2005 | Hedberg et al. |
| 2006/0067952 | A1 | 3/2006 | Chen |
| 2006/0141043 | A1 | 6/2006 | Lindfors |
| 2008/0193511 | A1 | 8/2008 | Massing |

FOREIGN PATENT DOCUMENTS

| | | |
|---|---|---|
| WO | 1999/04766 A1 | 2/1999 |
| WO | 2003/013472 A1 | 2/2003 |
| WO | 2004/043363 A2 | 5/2004 |
| WO | 2006/037089 A2 | 4/2006 |

OTHER PUBLICATIONS

Office Action from U.S. Appl. No. 12/309,581, dated Dec. 21, 2011.

Office Action from U.S. Appl. No. 12/309,581, dated Aug. 14, 2012.

Bissery et al., Docetaxel (Taxotere.RTM.): a review of preclinical and clinical experience. Part I: preclinical experience, Anti-Cancer Drugs, 6:339-368 (1995).

Bissery et al., Experimental Antitumor Activity of Taxotere (RP 56976, NSC 628503), a Taxol Analogue, Cancer Research, 51:4845-4852 (1991).

Davis et al., Ostwald Ripening and the Stability of Emulsion Systems: An Explanation for the Effect of an Added Third Component, Journal of Colloid and Interface Science, 80:508-511 (1981).

Dias et al., Pharmacokinetics and tumor uptake of a derivatized form of paclitaxel associated to a cholesterol-rich nanoemulsion (LDE) in patients with gynecologic cancers, Cancer Chemotherapy and Pharmacology, 59:105-111 (2006).

Dimitrova et al., Bulk Elasticity of Concentrated Protein-Stabilized Emulsions, Langmuir, 17:3235-3244 (2001).

Jain, Barriers to Drug Delivery in Solid Tumors, Scientific American, pp. 58-65 (1994).

Katsumata, Docetaxel: an alternative taxane in ovarian cancer, British Journal of Cancer 89 (Suppl 3), S9-S15 (2003).

Lacko et al., High Density Lipoprotein Complexes as Delivery Vehicles for Anitcancer Drugs, Anticancer Research, 22:2045-2050 (2002).

Rowinsky et al., The Clinical Pharmacology and Use of Antimicrotubule Agents in Cancer Chemotherapeutics, Pharmac. Ther., 52:35-84 (1991).

Sharma et al., Antitumor Effect of Taxol-containing Liposomes in a Taxol-resistant Murine Tumor Model, Cancer Research, 53:5877-5881 (1993).

Sharma et al., Novel Taxol Formulations: Preparation and Characterization of Taxol-Containing Liposomes, Pharmaceutical Research, 11:889-896 (1994).

\* cited by examiner

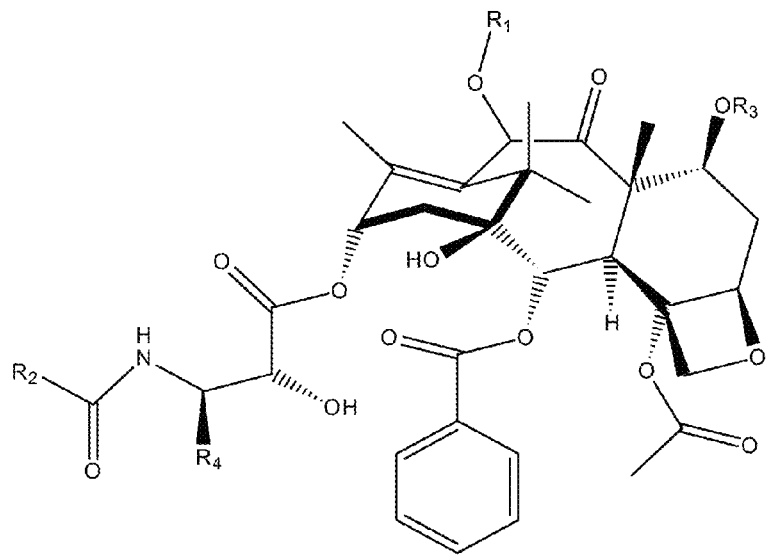
Paclitaxel R1 = COCH3 ; R2 = R4 =  ; R3 = H
Docetaxel R1 = H ; R2 = -OC(CH3)3 ; R3 = H; R4 = 
MAC-321 R1 = H ; R2 = -OC(CH3)3 ; R3 = CO-CH2-CH3; R4 = 
TL-909 R1 = -CO- ; R2 = -OC(CH3)2 ; R3 = H; R4 = 
TL-310 R1 = -CO- ; R2 = -OC-CH2-(CH3)2 ; R3 = H; R4 = 
Figure 1. Chemical Structure of Taxanes

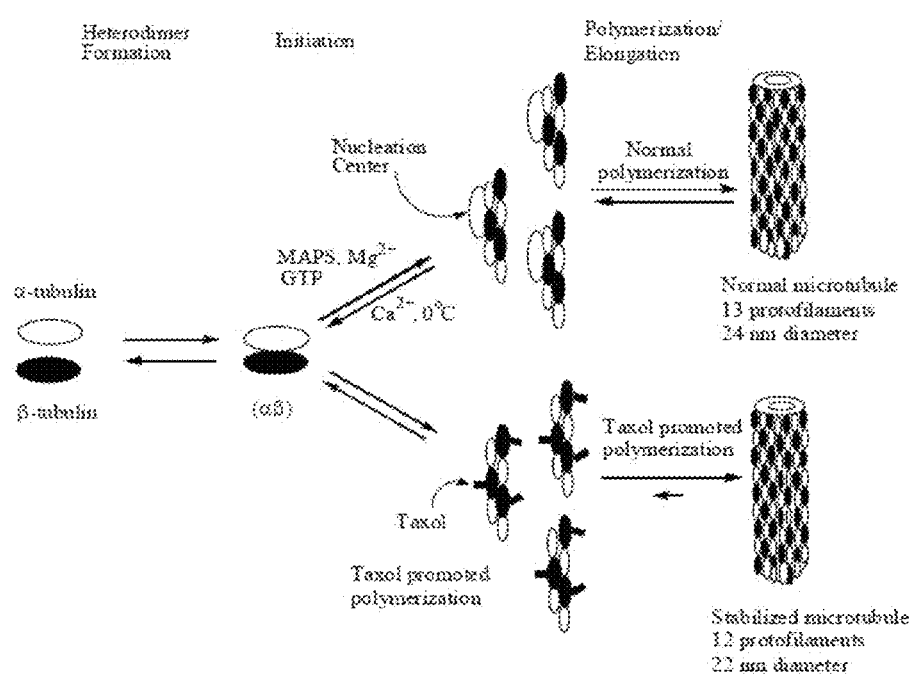
Figure 2. Tubulin-microtubule dynamics (Kingston 2001)

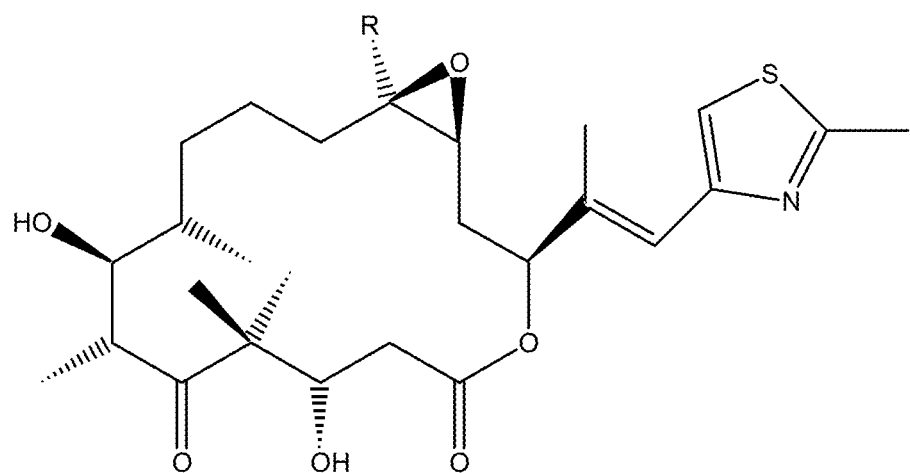
EPOTHILONE A  R = H
EPOTHILONE B  R = CH3
Figure 3. The Chemical Structure of Epothilone

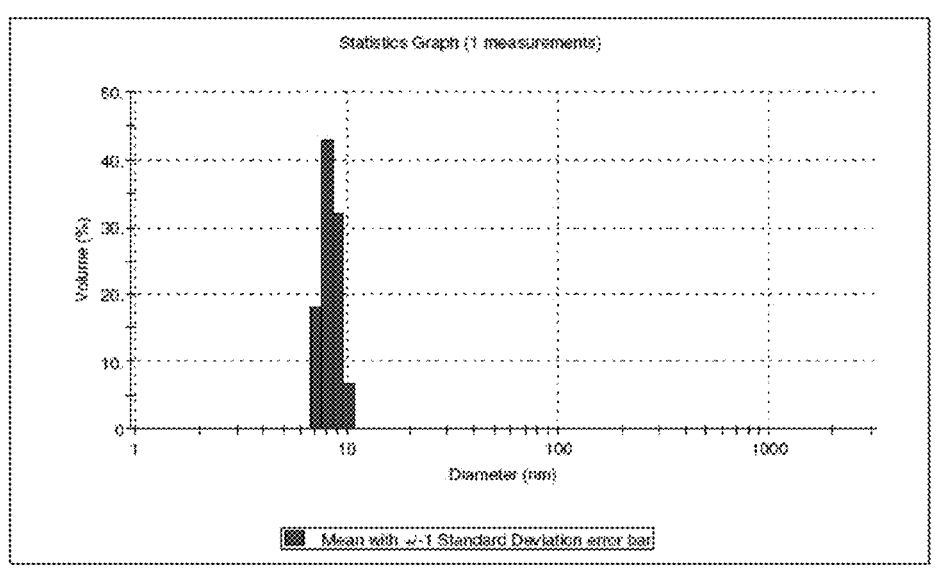
Figure 4. The Particle Size Analysis of 4% Albumin after Homogenization with Chloroform and Ethanol.

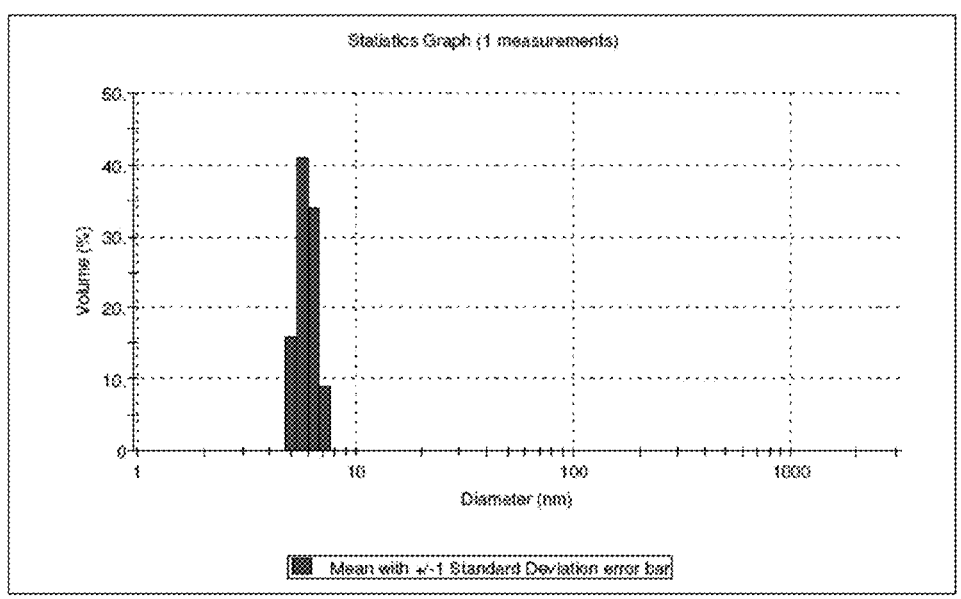
Figure 5. The Particle Size Analysis of 4% Albumin.

Figure 6. The particle size analysis of docetaxel containing cholesterol as inhibitor.
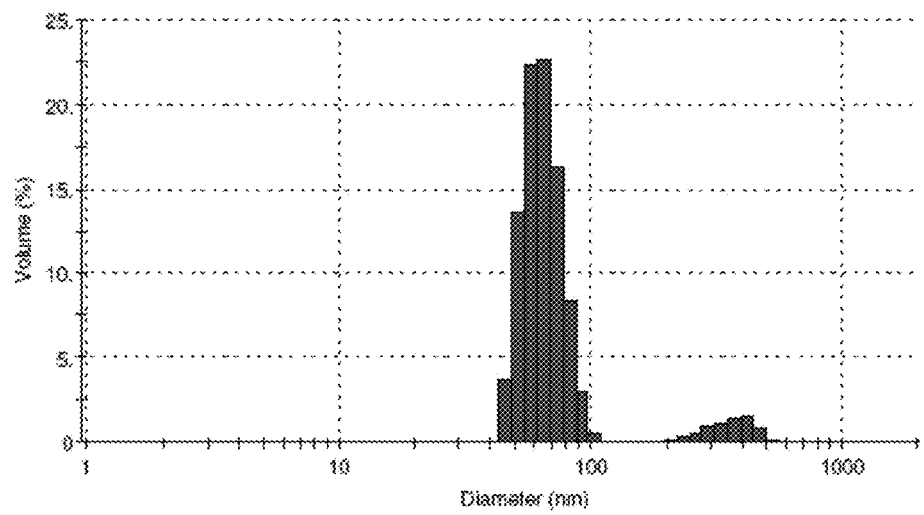
Figure 6(A). After Reconstitution
Figure 6(B). After 2 hours kept at 24 °C Figure 6 cont. The particle size analysis of docetaxel containing cholesterol as inhibitor.
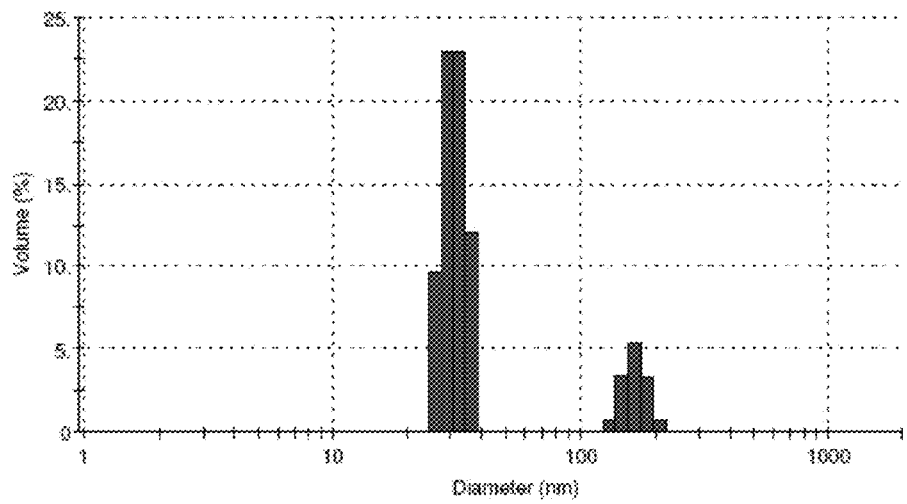
Figure 6(C). After 3 hour kept at 24 °C
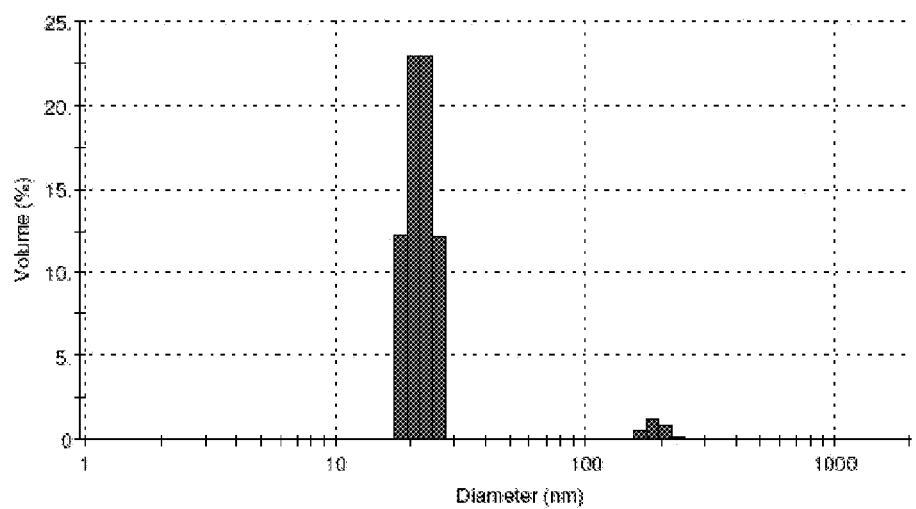
Figure 6(D). After 5 hour kept at 24 °C Figure 6 cont. The particle size analysis of docetaxel containing cholesterol as inhibitor.
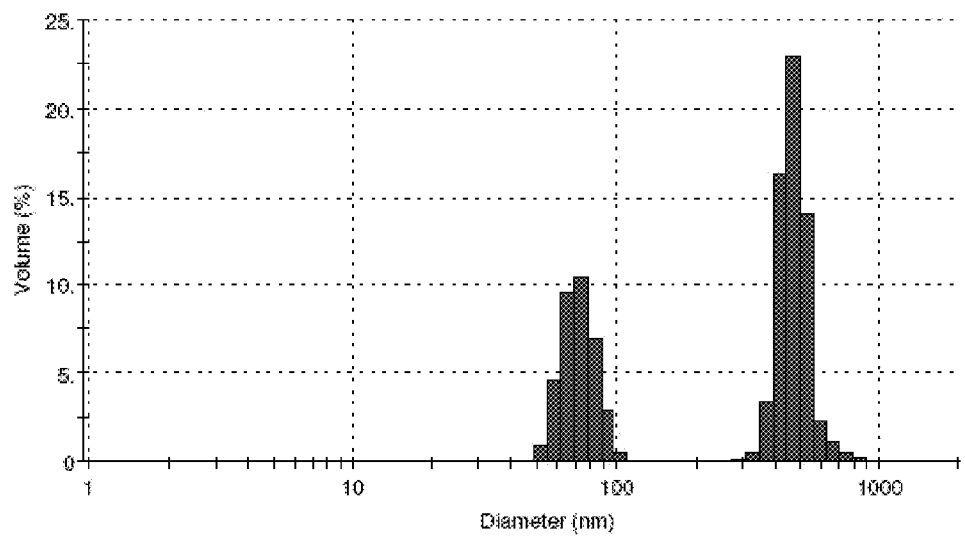
Figure 6(E). After 2 hrs kept at 2-6 °C
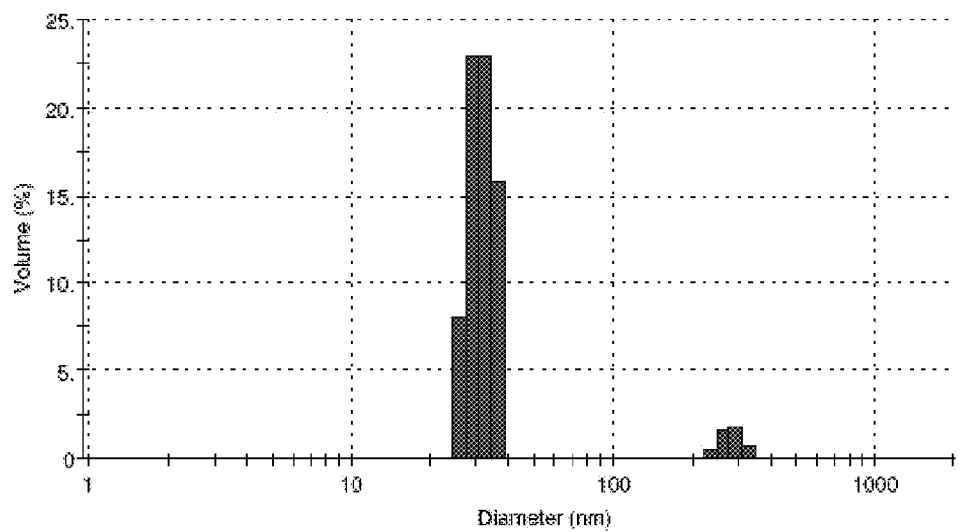
Figure 6(F). After 5 hour kept at 2-5 °C Figure 7. The particle size analysis of docetaxel containing cholesteryl stearate and cholesterol as inhibitors.
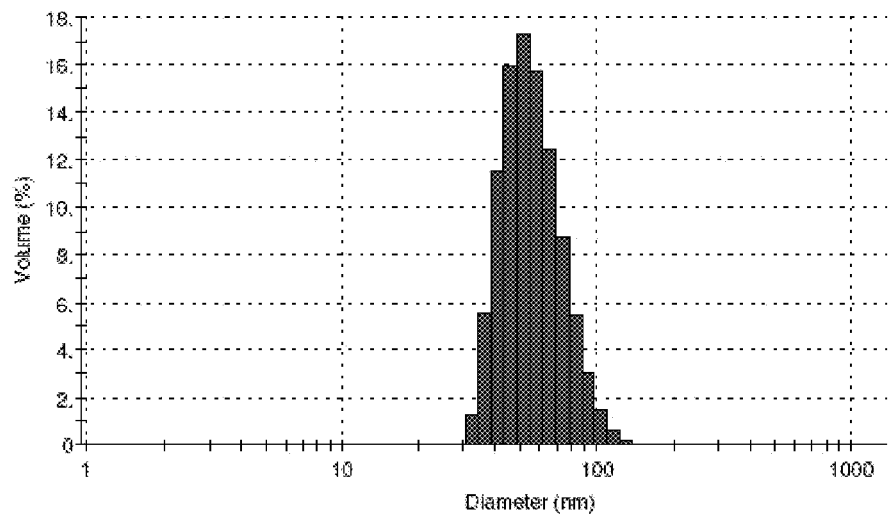
Figure 7(A). After reconstitution
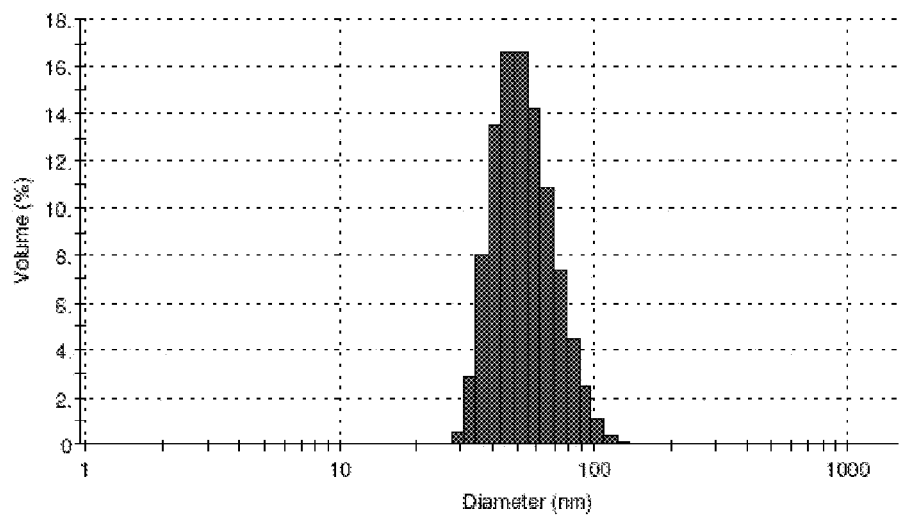
Figure 7(B). After 40 hrs kept at 24 °C Figure 7 cont. The particle size analysis of docetaxel containing cholesteryl stearate and cholesterol as inhibitors.
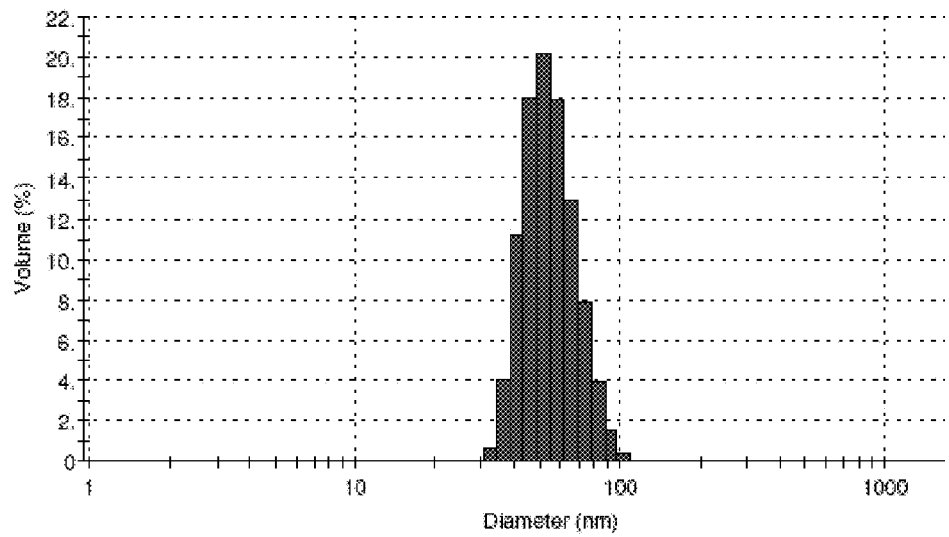
Figure 7(C). After 40 hrs kept at 2-6 °C
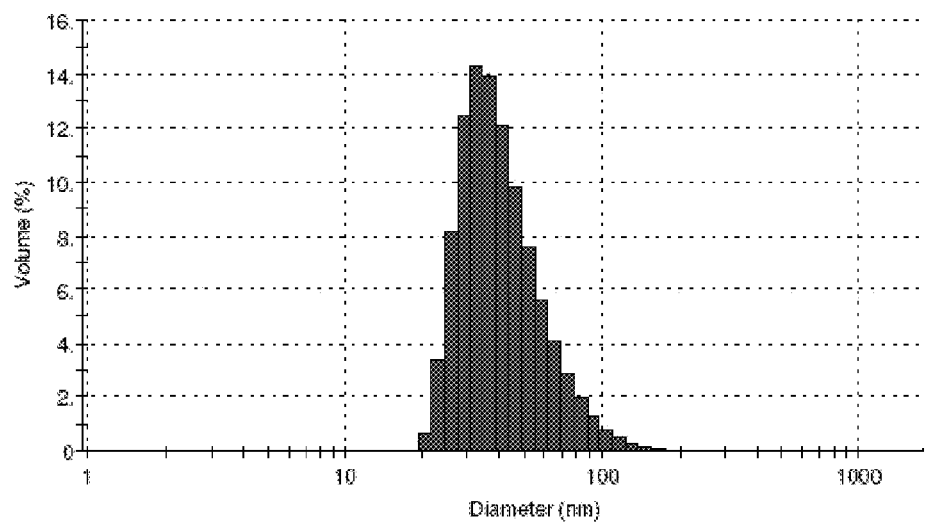
Figure 7(D). After 4 days kept at 2-6 °C Figure 7 cont. The particle size analysis of docetaxel containing cholesteryl stearate and cholesterol as inhibitors.
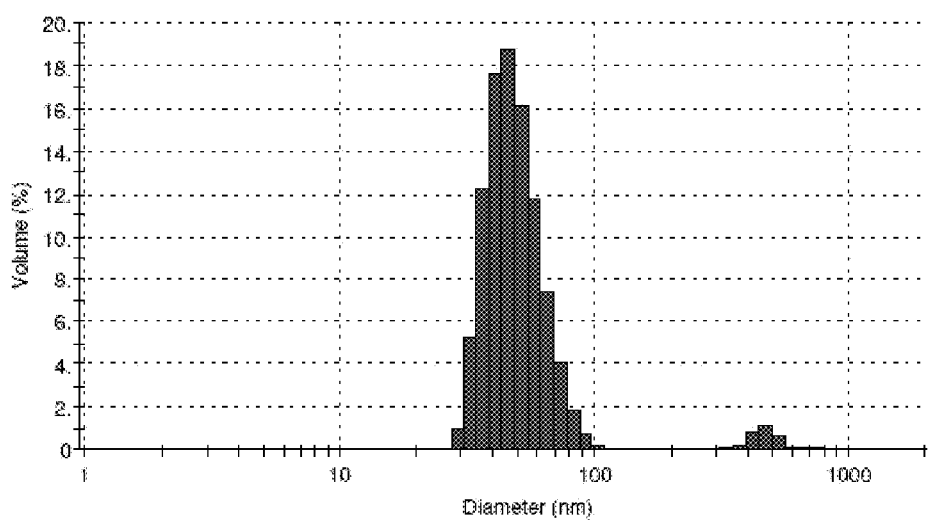
Figure 7(E). After 4 days kept 24 °C Figure 8. The particle size analysis of docetaxel containing hexadecyldexadecanoate and cholesterol as inhibitors.
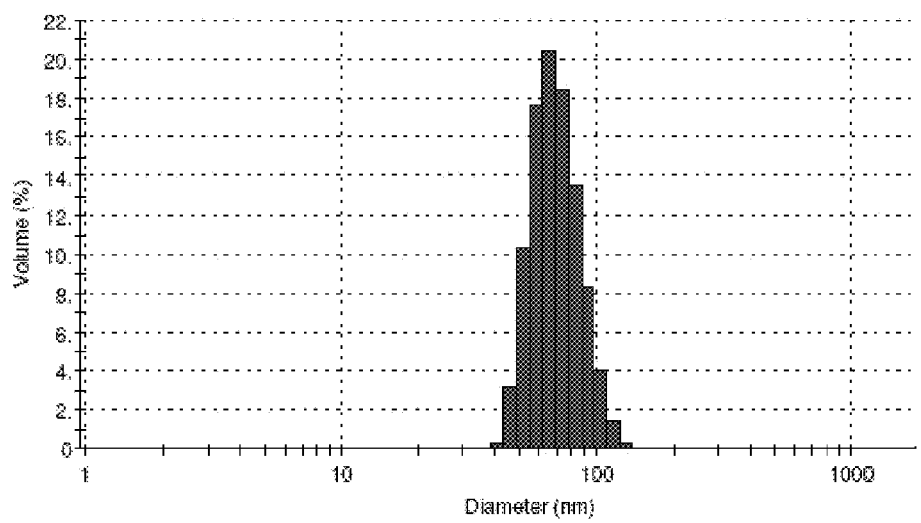
Figure 8(A). After reconstitution
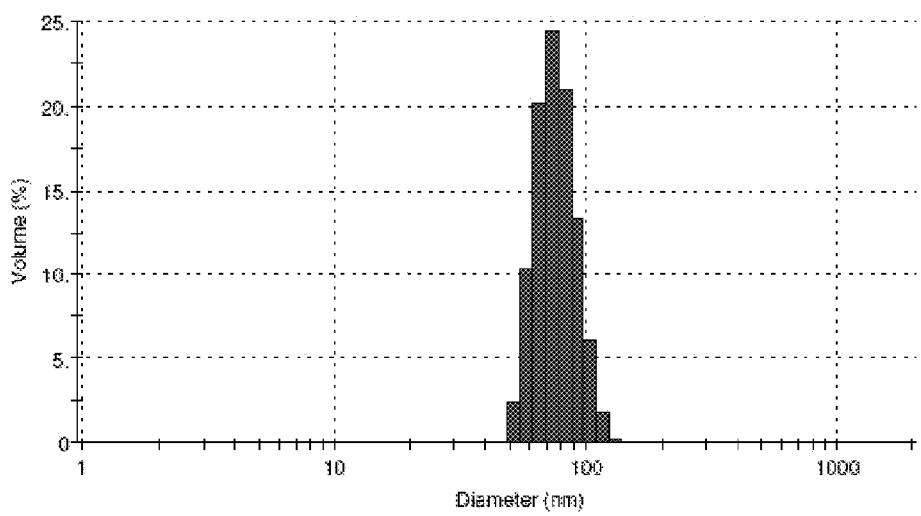
Figure 8(B). After 1 hour kept at 24 °C Figure 8 cont. The particle size analysis of docetaxel containing hexadecyldexadecanoate and cholesterol as inhibitors.
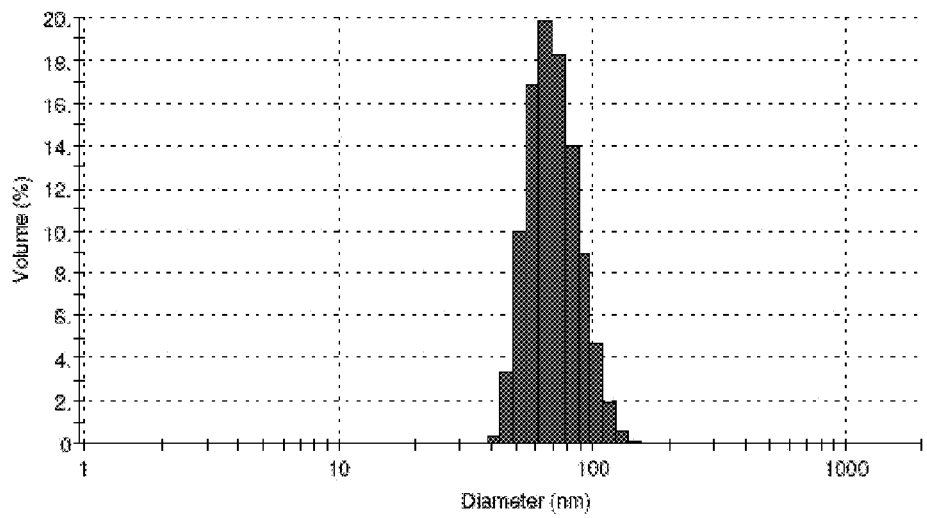
Figure 8(C). After 20 hrs kept at 24 °C
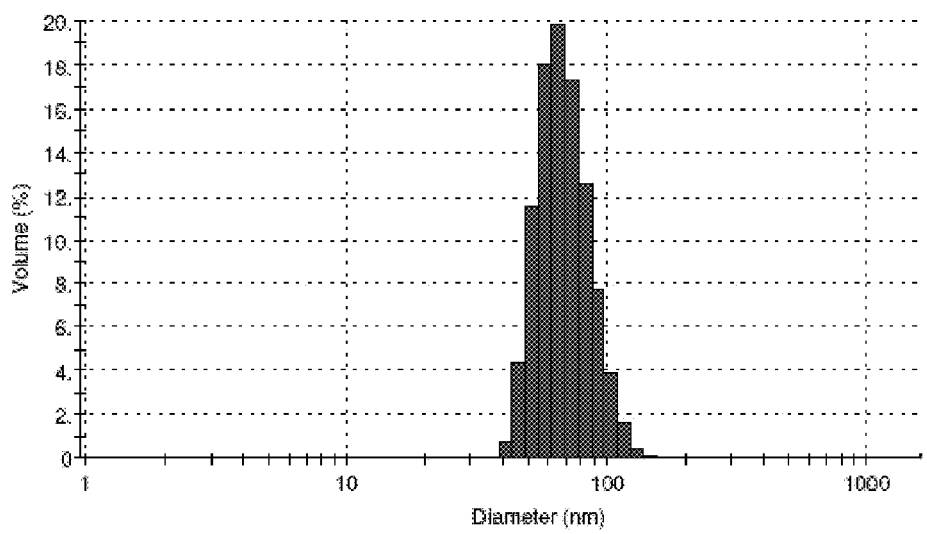
Figure 8(D). After 20 hrs kept at 2-6 °C Figure 8 cont. The particle size analysis of docetaxel containing hexadecyldexadecanoate and cholesterol as inhibitors.
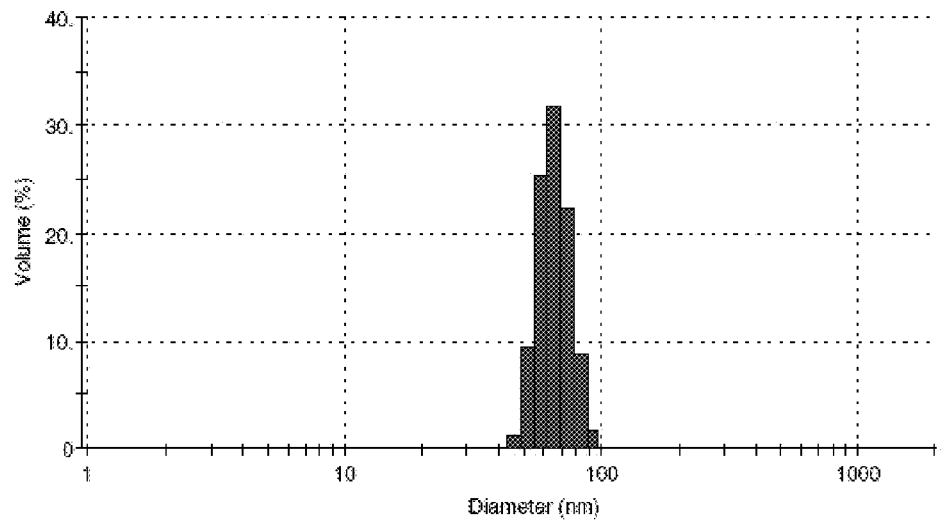
Figure 8(E). After 3 days kept at 24 °C
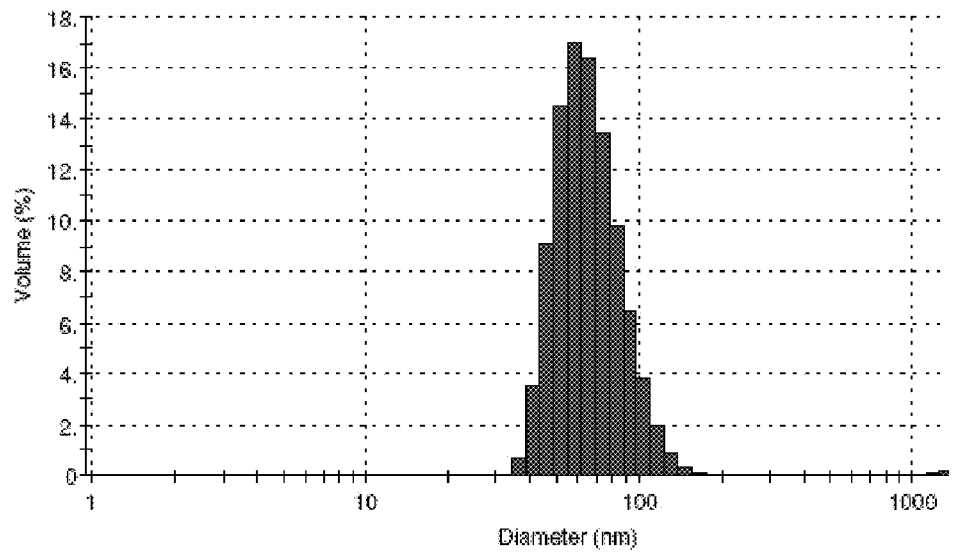
Figure 8(F). After 3 days kept at 2-6 °C Figure 8 cont. The particle size analysis of docetaxel containing hexadecyldexadecanoate and cholesterol as inhibitors.
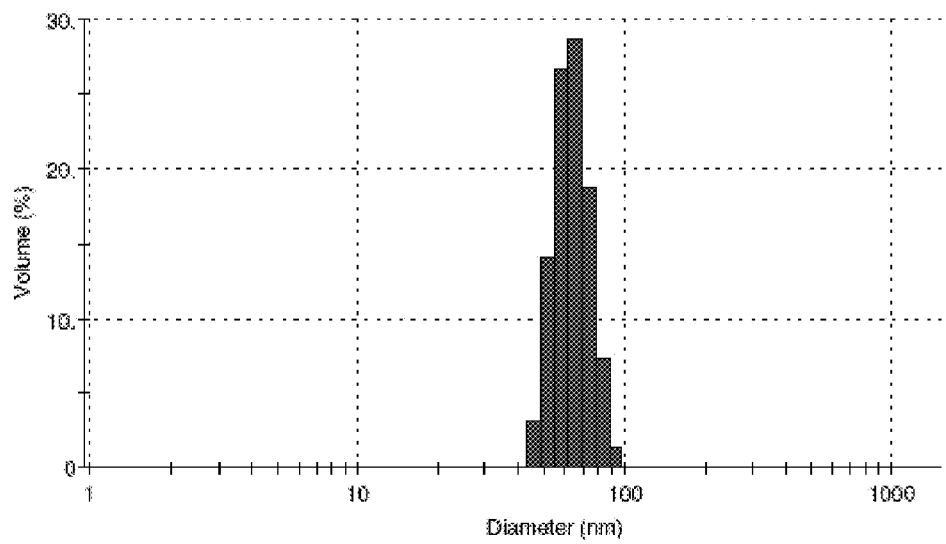
Figure 8(G). After 5 days kept at 24 °C
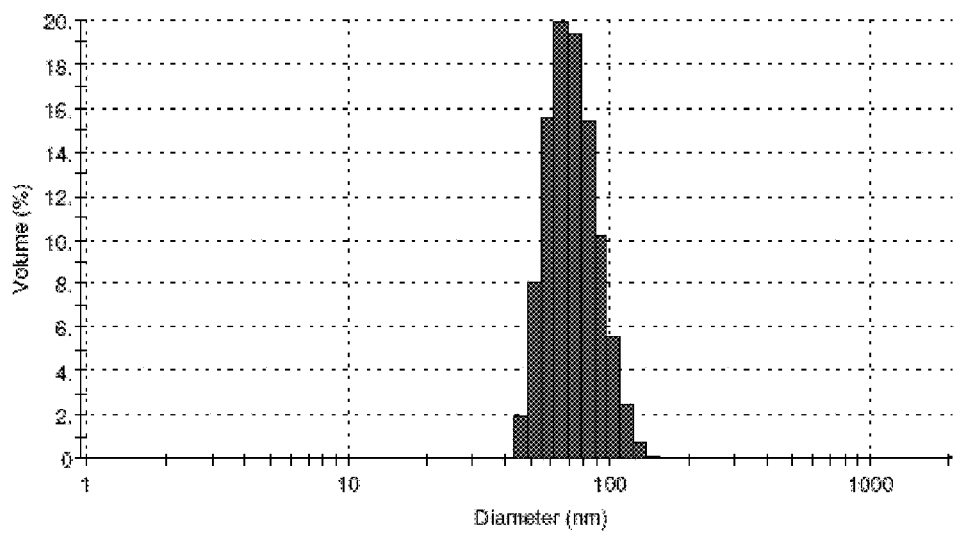
Figure 8(H). After 5 days kept at 2-6 °C Figure 9. The particle size analysis of docetaxel containing glyceryl tristearate and cholesterol as inhibitors.
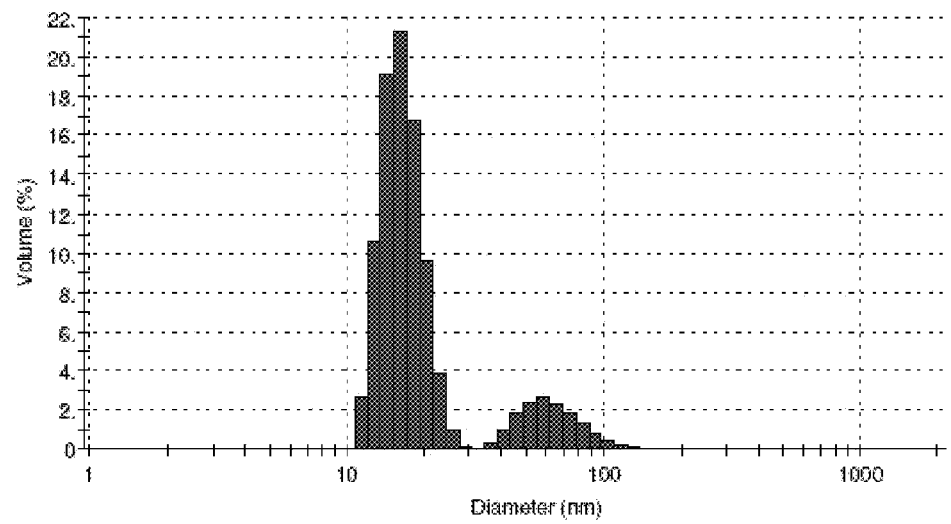
Figure 9(A). After reconstitution
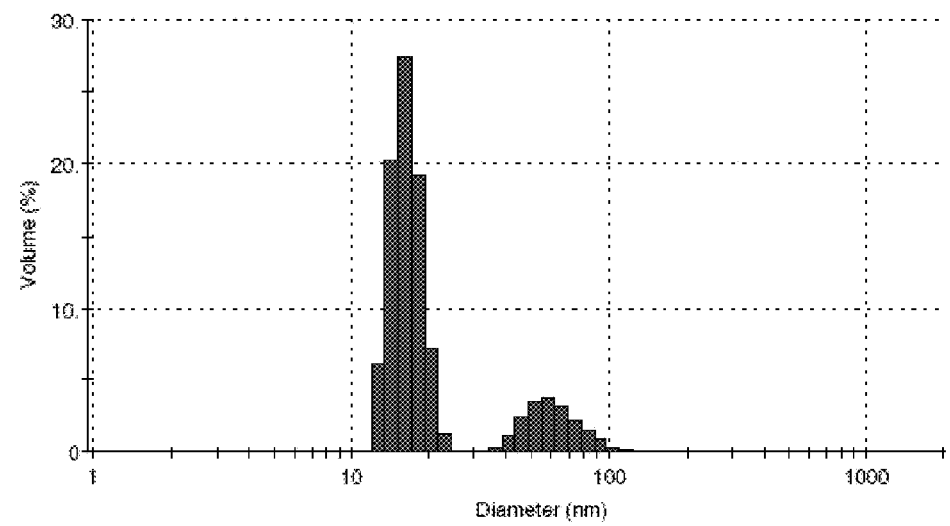
Figure 9(B). After 1 hr kept at 24 °C Figure 9 cont. The particle size analysis of docetaxel containing glyceryl tristearate and cholesterol as inhibitors.
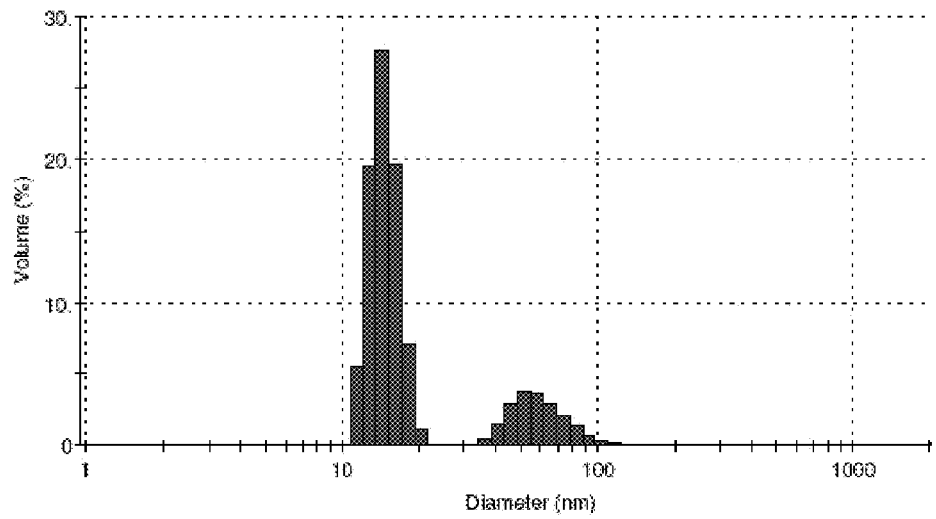
Figure 9(C). After 20 hrs kept at 24 °C
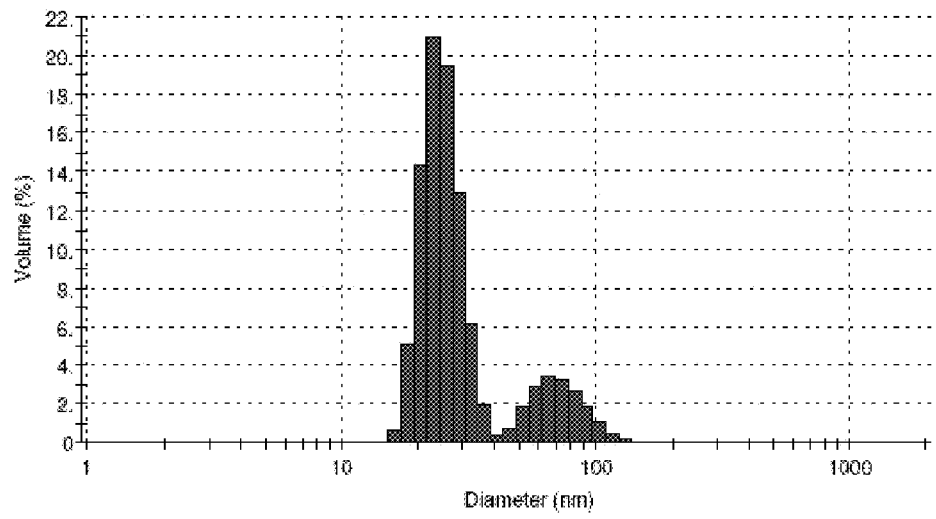
Figure 9(D). After 20 hrs kept at 2-6 °C Figure 9 cont. The particle size analysis of docetaxel containing glyceryl tristearate and cholesterol as inhibitors.
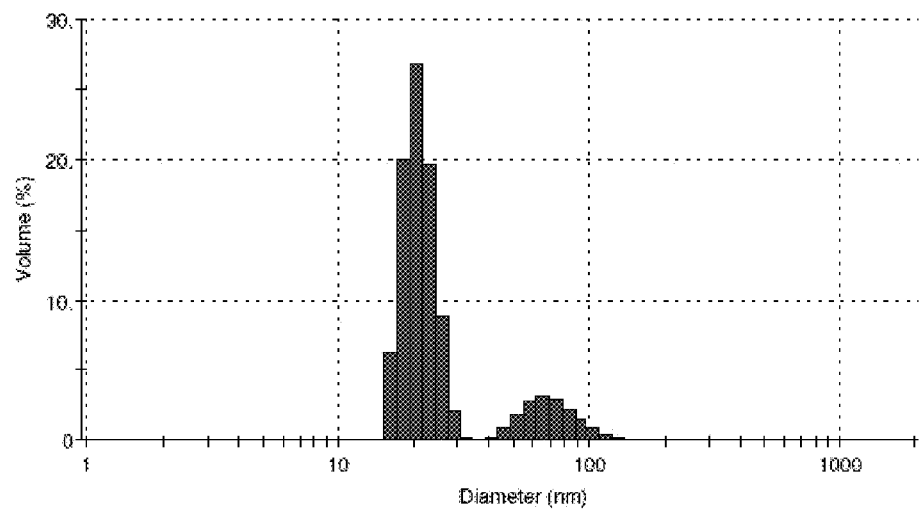
Figure 9(E). After 3 days kept at 24 °C
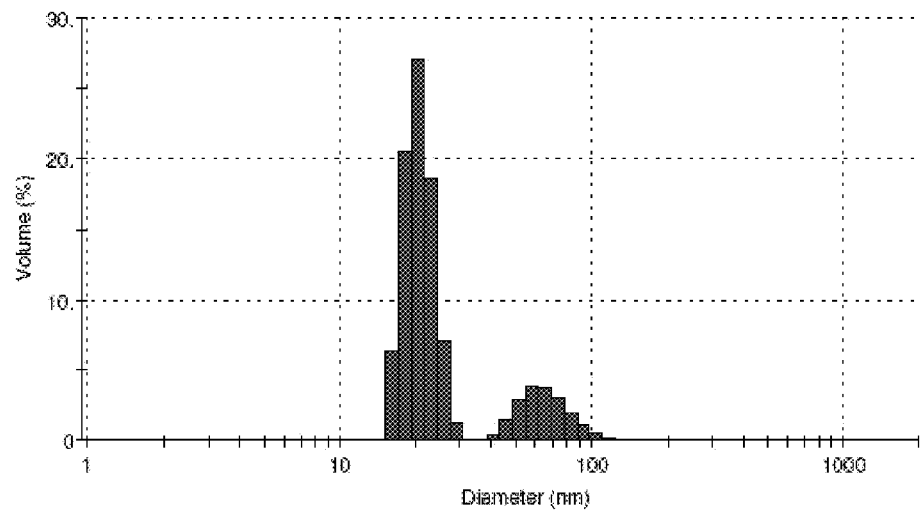
Figure 9(F). After 3 days kept at 2-6 °C Figure 9 cont. The particle size analysis of docetaxel containing glyceryl tristearate and cholesterol as inhibitors.
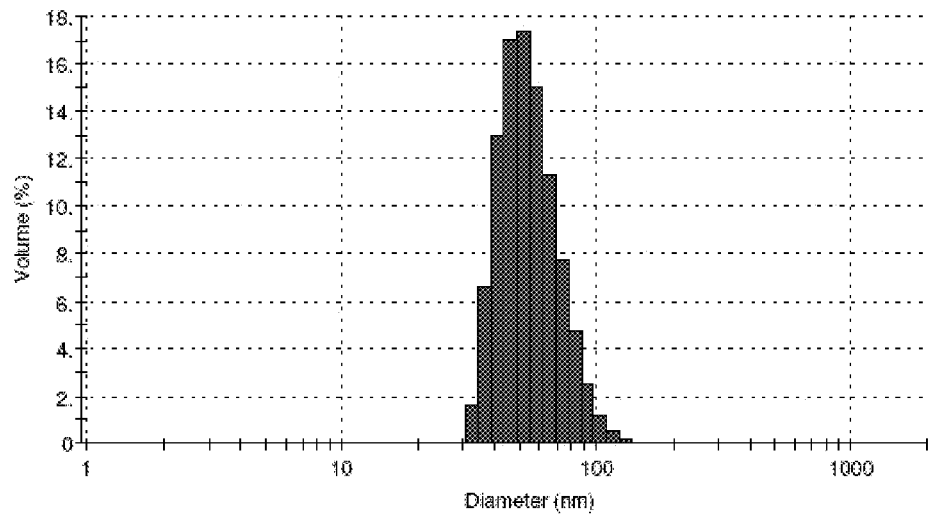
Figure 9(G). After 5 days kept at 24 °C
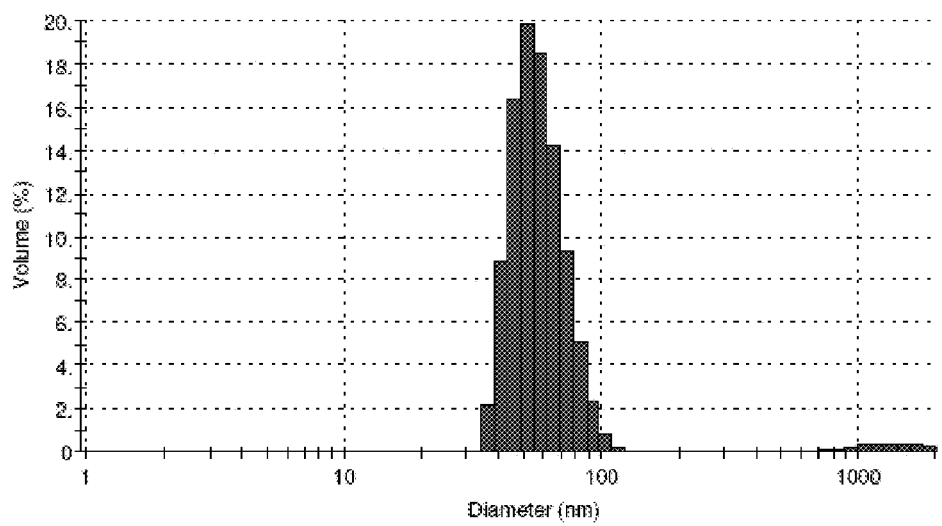
Figure 9(H). After 5 days kept at 2-6 °C Figure 10. The particle size analysis of docetaxel without any inhibitors.
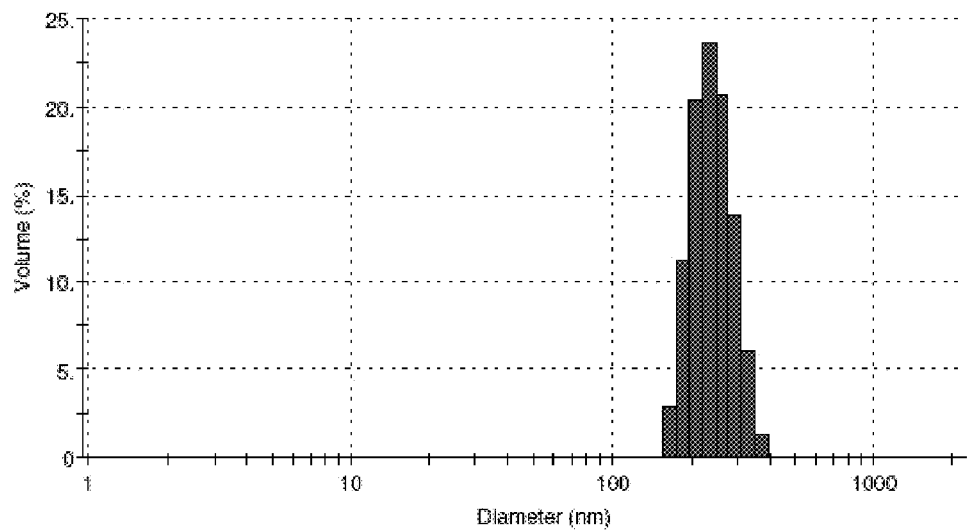
Figure 10(A). After reconstitution
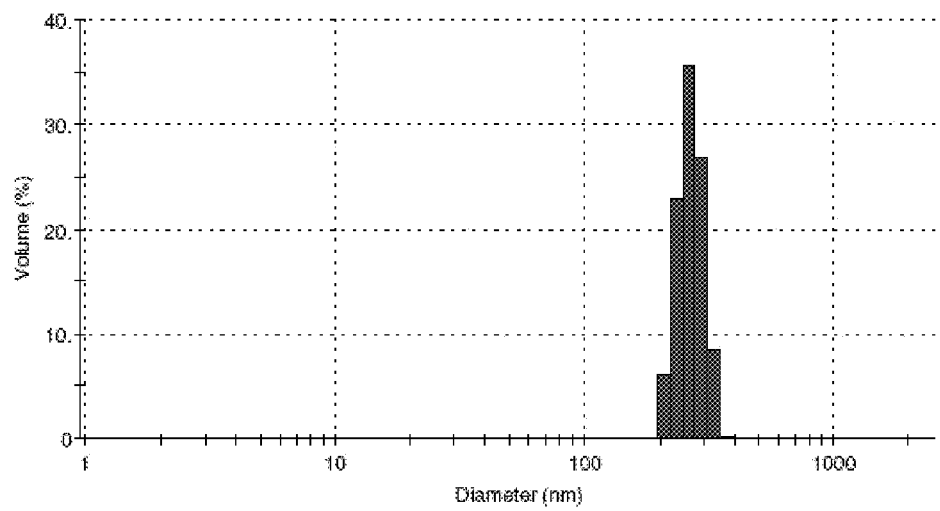
Figure 10(B). After 1hour kept at 24 °C Figure 11. Particle Size compared during the process of evaporation of the organic solvent.
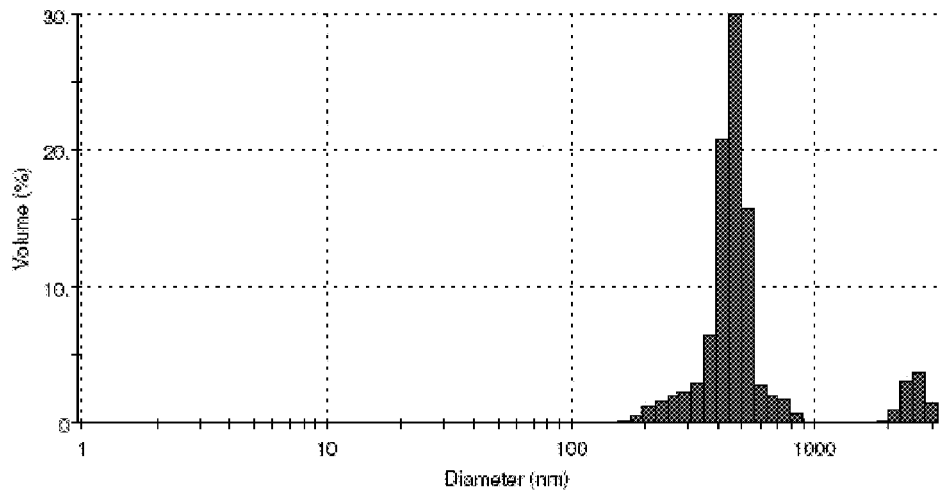
Figure 11(A). Particle Size immediately after the evaporation of the organic solvent
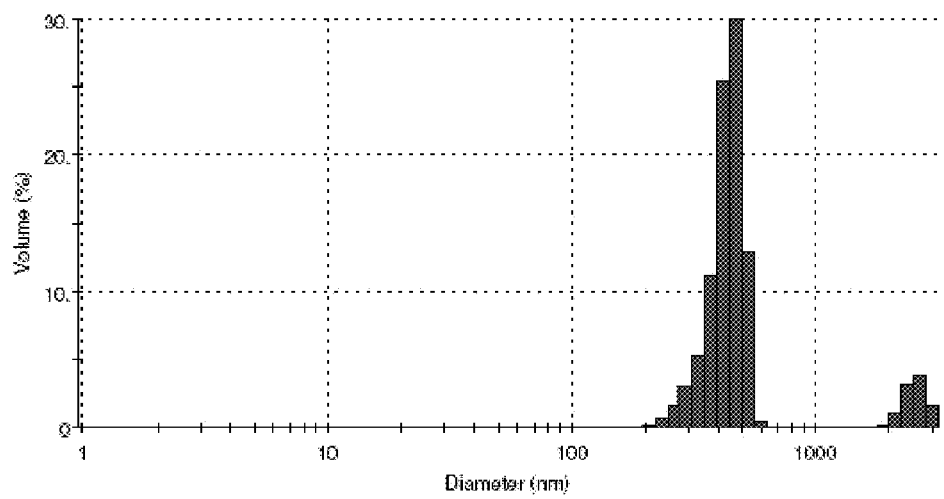
Figure 11(B). After 30 mins kept at 24 °C Figure 11 cont. Particle Size compared during the process of evaporation of the organic solvent.
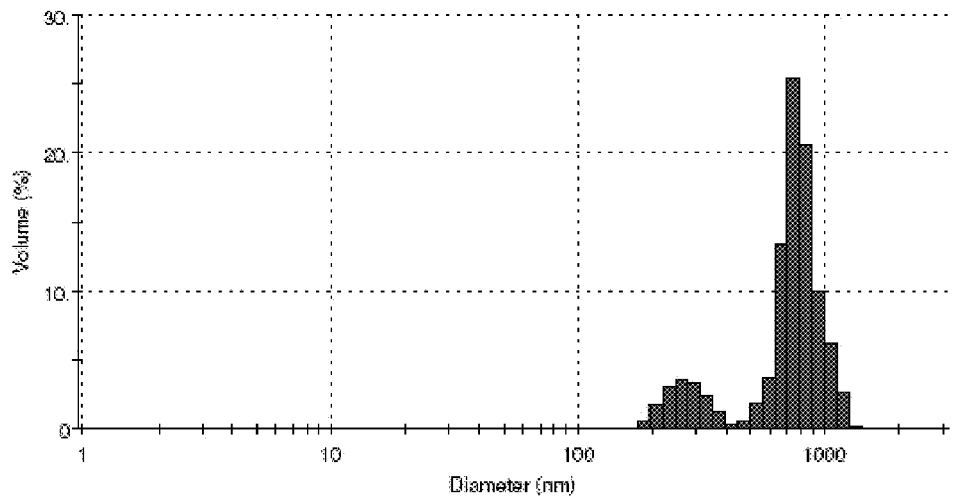
Figure 11(C). After 60 mins kept at 24 °C
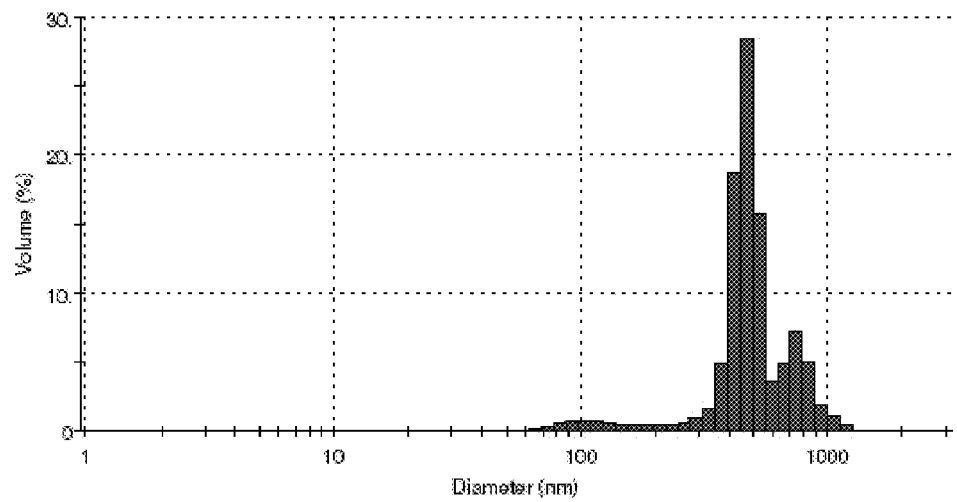
Figure 11(D). After 90 mins kept at 24 °C Figure 11 cont. Particle Size compared during the process of evaporation of the organic solvent.
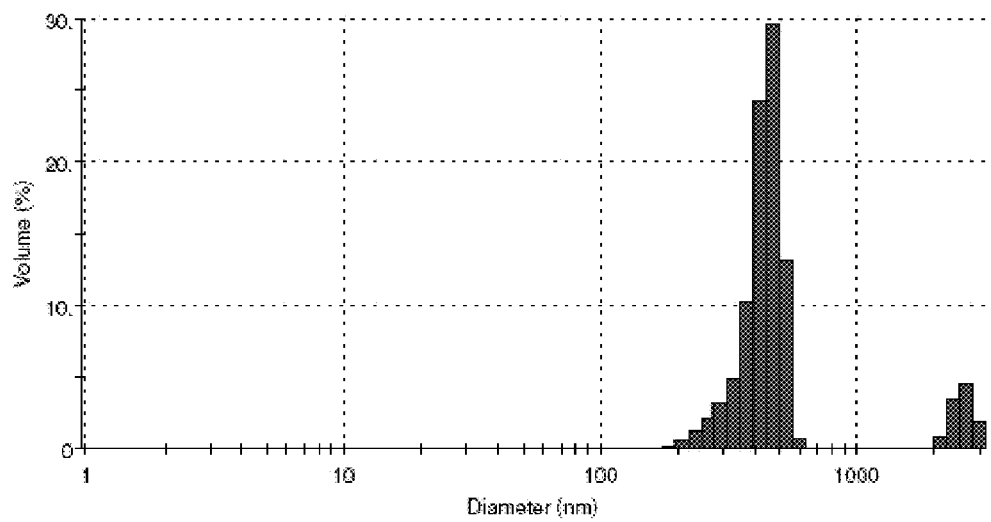
Figure 11(E). After 120 mins kept at 24 °C
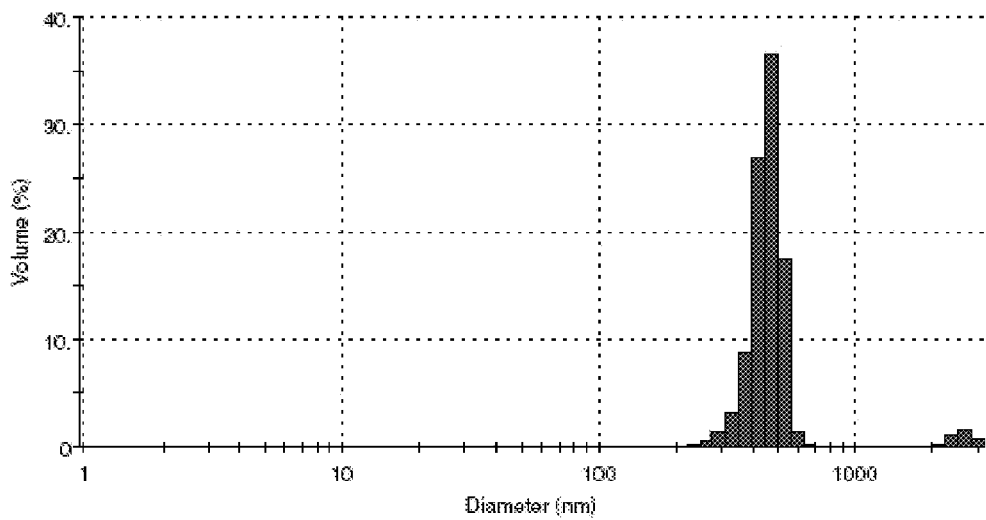
Figure 11(F). After 30 mins kept at 5 °C Figure 11 cont. Particle Size compared during the process of evaporation of the organic solvent.
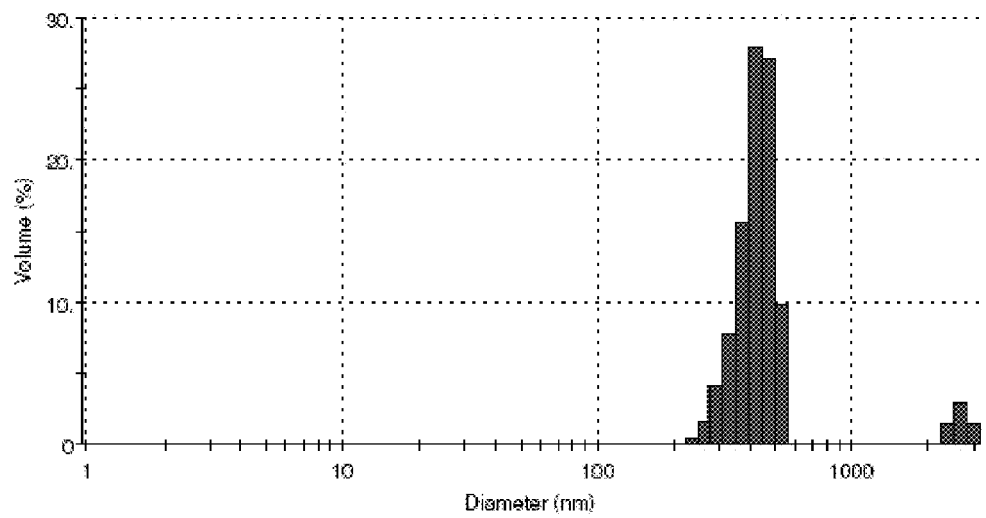
Figure 11(G). After 60 mins kept at 5 °C
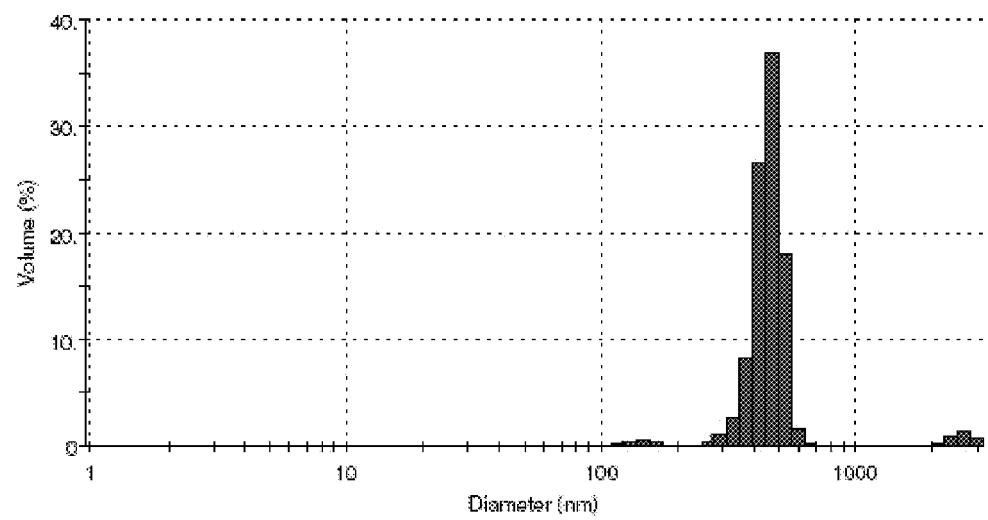
Figure 11(H). After 90 mins kept at 5 °C Figure 11 cont. Particle Size compared during the process of evaporation of the organic solvent.
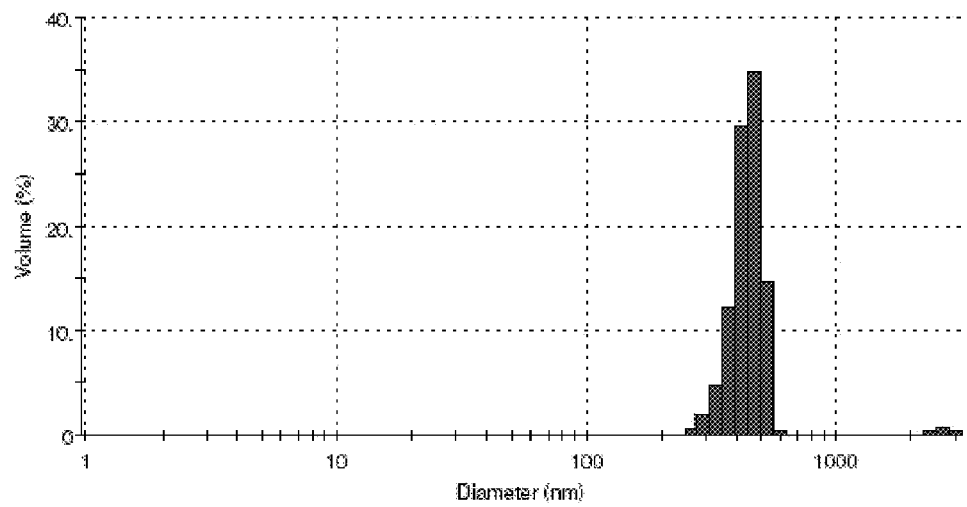
Figure 11(l). After 120 mins kept at 5 °C

SOLID NANOPARTICLE FORMULATION OF WATER INSOLUBLE PHARMACEUTICAL SUBSTANCES WITH REDUCED OSTWALD RIPENING

CROSS-REFERENCE TO RELATED APPLICATIONS

This application is a continuation of U.S. application Ser. No. 12/309,581, now U.S. Pat. No. 8,728,527, which is the U.S. National Stage Application under 35 U.S.C. § 371 of International Application No: PCT/US2007/016599, filed Jul. 24, 2007, which claims the benefit of U.S. Provisional Patent Application Ser. No. 60/832,587, filed Jul. 24, 2006.

TECHNICAL FIELD

This invention relates to a process for creating nanoparticles. More specifically it relates to a process for creating nanoparticles of a water insoluble substance so that the substance can dissolve in water. Even more specifically it relates to process for creating nanoparticles of a water insoluble pharmaceutical so that the pharmaceutical can be delivered in an aqueous medium.

BACKGROUND ART

The therapeutic efficacy of most anticancer agents is predicated on achieving adequate local delivery to the tumor site. Many cancer chemotherapeutic agents have been shown to be highly effective in vitro but not as effective in vivo. This disparity is believed to be attributable to, in part, the difficulty in delivering drug to the tumor site at therapeutic levels and the need for almost 100% cell kill to affect a cure (Jain 1994; Tannock 1998). Therapeutic molecules, cytokines, antibodies, and viral vectors are often limited in their ability to affect the tumor because of difficulty crossing the vascular wall (Yuan 1998). Inadequate specific delivery can lead to the frequently low therapeutic index seen with current cancer chemotherapeutics. This translates into significant systemic toxicities attributable to the wide dissemination and nonspecific action of many of these compounds.

Another problem is the solubility of some of the potent chemotherapeutic agents in suitable pharmaceutically acceptable vehicle for administration. Two classes of molecules widely used in chemotherapy are microtubule inhibitors such as taxane derivatives and topoisomerase I inhibitors such as campthothecin derivatives. However, it is now known as a fact that these two important classes of drugs have been formulated in vehicles which are very toxic to humans. The present invention is set to disclose novel pharmaceutical compositions to overcome the solubility and the vehicle toxicity problem of water insoluble pharmaceutical substances.

Microtuble Inhibitors as Therapeutic Agents:

Paclitaxel (Taxol, FIG. 1) is a natural diterpene product isolated from the pacific yew tree (*Taxus brevifolia*) by Wani et al (1971). The taxanes, paclitaxel and docetaxel (U.S. Pat. No. 4,814,470), belong to a novel class of anticancer drugs that stabilize microtubules and lead to tumor cell death. Paclitaxel (Taxol®, Bristol-Myers Squibb Co., NJ, USA), the first microtubule stabilizer identified, has proved to be of great value for the treatment of many types of cancer (Rowinsky 2001, Holton 1995). The clinical successes of paclitaxel led to the development of a second-generation taxane, docetaxel (Taxotere®, Sanofi-Aventis Pharmaceuticals, NJ, USA), and initiated the intense search for other compounds with a similar mechanism of action. Several classes of structurally diverse microtubule-stabilizing compounds have been identified. The nontaxane stabilizers identified, the epothilones (Bollag 1995), Taccalonolides (Tinley 2003) and discodermolide (Mooberry 2004 and 1999; Martello 2000), had excellent preclinical activities and are being evaluated in clinical trials as anticancer agents.

Microtubules are tubulin polymers involved in many cellular functions (Dustin 1984), one of which being the formation of the mitotic spindle required for chromosome moving to the poles of the new forming cells during cell division (Avila 1990). The importance of microtubules to cellular functions makes them a sensitive target for biological microtubule poisons. All compounds that interact with microtubules in the sense of their stabilization or disorganization are called microtubule inhibitors. They have cytotoxic effect and may kill the cell. Since microtubules are required to carry out mitosis in cell proliferation, microtubule inhibitors would primarily attack cancer cell which divides more frequently than healthy cell. Therefore many of them are very important anti-cancer compounds.

Tubulin is a protein whose quaternary structure is composed of two polypeptide subunits, α- and β-tubulin. Several isotypes have been described for each subunit in higher eucaryots. Microtubule functions are based on their capacity to polymerize and to depolymerize. This process is a very dynamic and is attend with rapid shortening or elongation of this cell structures. Tubulin is a GTP-binding protein and the binding of this nucleotide to the protein is required for microtubule polymerization, whereas the hydrolysis of the GTP bound to polymerized tubulin is required for microtubule depolymerization. Microtubule stability in healthy cell is regulated by the presence of some proteins called microtubule-associated proteins (MAP) which facilitate microtubule stabilization. The cellular mechanisms regulating microtubule assembly is highly sensitive to the concentration of $Ca^{2+}$. The low cytosolic $Ca^{2+}$ level characteristic of the resting state of most eucaryotic cells promotes microtubule assembly, while the localized increase in $Ca^{2+}$ cause microtubule disassembly (Gelford 1991). Microtubules form through polymerization of protein dimers, consisting of one molecule each of α- and β-tubulin. Dimer and polymer are in a state of dynamic equilibrium, so that the network can respond flexibly and quickly to functional requirements. The polymer forms a fine, unbranched cylinder, usually with internal and external diameters of 14 and 28 nm, respectively, the so called microtubule (FIG. 2; Kingston 2001). Assembly is initiated by the binding together of α, β-dimers to form short protofilaments, 13 of which subsequently arrange themselves side by side to form the microtubule. Subsequent growth of the microtubule is polar, occurring mainly at the so-called plus end of the protofilaments through the addition of further dimers. Addition involves GTP, which is bound to the dimer, being cleaved to GDP, which remains attached to the tubulin. The binding site for GTP is on the b-subunit. When the cell becomes enriched with GTP-tubulin dimers, hydrolysis to GDP-tubulin falls behind the rate of assembly and a α, β-tubulin-GTP cap forms at the plus end of the protofilaments blocking further growth of the microtubule.

Microtubule inhibitors represents chemically very variegated group of compounds from different biological sources with strong effect on cytoskeletal functions and strong toxicity. Microtubule functions in cell depend on the capacity of tubulin to polymerize or the capacity of microtubules to depolymerize. Compounds which are able to influent these processes, i.e. microtubule inhibitors (also anti-tubulin agents, antimitotic agents, etc.), can be divided into four group according to their mechanism of action. 1. Compounds which bind to GTP site; 2. compounds which bind to colchicine site; 3. compounds which influence as microtubule-stabilizing agents; and 4. Compounds which do microtubule network disorganization.

In the structure of taxol there are two aromatic rings and a tetracyclic-structure containing an oxetane ring which is required for the activity of the drug. The primary action of this compound is to stabilize microtubules, preventing their depolymerization (FIG. 2). In this way taxol should block proliferating cells between G2 and mitosis, during the cell cycle. The binding of taxol appears to occur at different localizations at the amino terminal of β-tubulin, but binding to the middle region of an α-tubulin has also been reported (Loeb 1997).

A new class of microtubule-stabilizing compounds has been isolated from the bacterium Sorangium cellulosum. These macrolide compounds were called epothilones (FIG. 3), because their typical structural units are epoxide, thiazole, and ketone (Kowalski 1997; Schinzer 1996). Epothilone occurs in two structural variations, epothilone A and epothilone B, the latter containing an additional methyl group (Hyfle 1996). Epothilone A is the main product of bacteria metabolism, the yield of epothilone B amounting to 20-30 percent of the yield of epothilone A. Despite the small different in chemical structure, in most test systems epothilone B has been approximately ten-time more effective. These compounds show a striking effect on stabilizing polymerization of microtubules and they are easily obtained on large scale by a fermentation process (Gerth 1994). Both epothilones show a very narrow spectrum of activity and halts cells, as does taxol, in the G2-M phase. The Total synthesis of epothilones was reported in many laboratories (Balog 1996; Su 1997; Yang 1997; Schinzer 1997).

Interesting semisynthetic analogue of taxol with clinical use is docetaxel (Taxotere; FIG. 2), compound which contains a taxane ring linked to an oxetan ring at positions C-4 and C-5 and to an ester side chain at C-13.

Despite its broad clinical utility, there has been difficulty formulating paclitaxel and docetaxel because of their insolubility in water. The aqueous solubility of paclitaxel is only about 12 mg/liter. Paclitaxel and docetaxel are also insoluble in most pharmaceutically-acceptable solvents, and lack a suitable chemical functionality for formation of a more soluble salt. Consequently, special formulations are required for parenteral administration of paclitaxel and docetaxel. Paclitaxel and docetaxel are very poorly absorbed when administered orally (less than 1%). No oral formulation of paclitaxel has obtained regulatory approval for administration to patients.

Paclitaxel is currently formulated as Taxol®, which is a concentrated nonaqueous solution containing 6 mg paclitaxel per mL in a vehicle composed of 527 mg of polyoxyethylated castor oil (Cremophor® EL) and 49.7% (v/v) dehydrated ethyl alcohol, USP, per milliliter (available from Bristol-Myers Squibb Co., NJ, USA). Cremophor EL improves the physical stability of the solution, and ethyl alcohol solubilizes paclitaxel. The solution is stored under refrigeration and diluted just before use in 5% dextrose or 0.9% saline. Intravenous infusions of paclitaxel are generally prepared for patient administration within the concentration range of 0.3 to 1.2 mg/mL. In addition to paclitaxel, the diluted solution for administration consists of up to 10% ethanol, up to 10% Cremophor EL and up to 80% aqueous solution. However, dilution to certain concentrations may produce a supersaturated solution that could precipitate. An inline 0.22 micron filter is used during Taxol® administration to guard against the potentially life-threatening infusion of particulates.

Docetaxel is currently formulated as Taxotere®, which is a concentrated nonaqueous solution containing 40 mg docetaxel per mL in a vehicle composed of 1040 mg of polysorbate 80 and is diluted with 13% (v/v) dehydrated ethyl alcohol in water for injection (available from Sanofi-Aventis Pharmaceuticals Inc., NJ, USA). The first stage-diluted solution is further diluted just before use in 5% dextrose or 0.9% saline. Intravenous infusions of docetaxel are generally prepared for patient administration within the concentration range of 0.3 and 0.74 mg/mL. However, dilution to certain concentrations may produce a supersaturated solution that could crystallize and precipitate. An inline 0.22 micron filter is used during Taxotere® administration to guard against the potentially life-threatening infusion of particulates.

Several toxic side effects have resulted from the administration of docetaxel in the Taxotere® formulations including anaphylactic reactions, hypotension, angioedema, urticaria, peripheral neuropathy, arthralgia, mucositis, nausea, vomiting, alopecia, alcohol poisoning, respiratory distress such as dyspnea, cardiovascular irregularities, flu-like symptoms such as myalgia, gastrointestinal distress, hematologic complications such as neutropenia, genitourinary effects, and skin rashes. Some of these undesirable adverse effects were encountered in clinical trials, and in some cases, the reaction was fatal. To reduce the incidence and severity of these reactions, patients are pre-medicated with corticosteroids, diphenhydramine, H2-antagonists, antihistamines, or granulocyte colony-stimulating factor (G-CSF), and the duration of the infusion has been prolonged. Although such pre-medication has reduced the incidence of serious hypersensitivity reactions to less than 5%, milder reactions are still reported in approximately 30% of patients. All patients treated with Taxotere® are required to be pre-medicated with oral corticosteroids, such as dexamethasone 16 mg per day for 3 days starting 1 day prior to Taxotere® administration, to reduce the incidence and severity of fluid retention as well as the severity of hypersensitivity reactions Different strategies have been pursued to produce safer and better-tolerated taxane compositions than the current ones. Alternative formulations of paclitaxel and docetaxel that avoid the use of Cremophor and polysorbate 80 have been proposed.

Phospholipid-based liposome formulations for paclitaxel, docetaxel, and other active taxanes have been developed (Sharma et al. 1993; Sharma and Straubinger 1994), and the physical properties of these and other taxane formulations have been studied (Sharma and Straubinger 1994; Balasubramanian 1994; Balasubramanian 1994). The main utility of these formulations is the elimination of toxicity related to the Cremophor EL excipient, and a reduction in the toxicity of the taxane itself, as demonstrated in several animal tumor models (Sharma 1993; A. Sharma 1995; Sharma 1996). This observation holds for several taxanes in addition to paclitaxel (Sharma 1995). In some cases, the antitumor potency of the drug appears to be slightly greater for the liposome-based formulations (Sharma 1993).

U.S. Pat. No. 6,348,215 discloses a method of stabilizing a taxane in a dispersed system, which method comprises exposing the taxane to a molecule which improves physical stability of the taxane in the dispersed system. By improving the physical stability of the taxane in the dispersed system, higher taxane content can be achieved. The patent provides a stable taxane-containing liposome preparation comprising a liposome containing one or more taxanes present in the liposome in an amount of less than 20 mol % total taxane to liposome, wherein the liposome is suspended in a glycerol: water composition having at least 30% glycerol.

U.S. Pat. Nos. 5,439,686, 5,560,933 and 5,916,596 disclose compositions for the in vivo delivery of substantially water insoluble pharmacologically active substances (such as the anticancer drug taxol) in which the pharmacologically active agent is delivered in a soluble form or in the form of suspended particles. In particular, the soluble form may comprise a solution of pharmacologically active agent in a biocompatible dispersing agent contained within a protein walled shell. Alternatively, the protein walled shell may contain particles of taxol. The polymeric shell is a biocompatible polymer, such as albumin, cross-linked by the presence of disulfide bonds. The polymeric shell, containing substantially water insoluble pharmacologically active substances therein, is then suspended in a biocompatible aqueous liquid for administration. The process for making such a polymeric shell is by emulsification of the drug alone dissolved in a nonpolar solvent such as chloroform and an aqueous solution of albumin and rapidly evaporating the emulsion around 50° C. According to the patents the process is producing cross-linked polymeric protein shell of albumin by the formation of disulfide bonds between albumin molecules and the drug is inside the polymeric shell as in a container. Further the patents distinguish the invention from protein microspheres formed by chemical cross linking and heat denaturation methods due to the formation of specific disulfide bonds with minimal denaturation of the protein. In addition, particles of substantially water insoluble pharmacologically active substances contained within the polymeric shell differ from cross-linked or heat denatured protein microspheres of the prior art because the polymeric shell produced by the process is relatively thin compared to the diameter of the coated particle.

However, it is known in the prior art that in oil-in-water emulsion using protein as emulsifying agent, certain amount of the protein may be denatured due to the interaction of the protein with the interface region between oil and water and the denatured protein may aggregate to form larger particle size due to the lower solubility of denatured protein as compared to native protein (Hegg 1982). The rest of the protein would stay in the aqueous phase as monomer. This can be demonstrated by the fact that the rapid evaporation of an oil-in-water microemulsion made by homogenization of chloroform in 2-5% albumin solution produce a hazy protein solution after evaporation around 50° C. and more than 95% of the protein is present in the solution either as monomer or dimer as measured by particle size analyzer. In other words, the protein can be recovered in a soluble form without any appreciable cross linking. Further it has been shown that disulfide cross-linking is not a determining factor in the gel formation of globular proteins (Hegg 1982) and molecular aggregations at the interface are important for emulsion stability (Dimitrova 2001). Thus the U.S. Pat. No. 5,439,686 may refer the formation of amorphous taxol nanoparticles surrounded by albumin molecules on the surface as encapsulated taxol in a protein polymeric shell formed by cross linking of the —SH groups in the protein.

Further, according to the U.S. Pat. No. 5,439,686 and U.S. Pat. No. 5,916,596, unlike conventional methods for nanoparticle formation, a polymer (e.g. polylactic acid) is not dissolved in the oil phase. The oil phase employed in the preparation of the disclosed compositions contains only the pharmacologically active agent dissolved in solvent. This is important because the U.S. Pat. No. 5,439,686 and U.S. Pat. No. 5,916,596 focused exclusively dissolving only the pharmacologically active agent and nothing else in the oil phase.

Using the technology disclosed by U.S. Pat. No. 5,439,686, a commercially viable paclitaxel formulation has been made and has been approved by the FDA for human use in 2005. It is marketed as ABRAXANE® (American Pharmaceuticals Partners Inc., IL, USA). The product description claims that ABRAXANE® for Injectable Suspension (paclitaxel protein-bound particles for injectable suspension) is an albumin-bound form of paclitaxel with a mean particle size of approximately 130 nanometers. ABRAXANE® is supplied as a white to yellow, sterile, lyophilized powder for reconstitution with 20 mL of 0.9% Sodium Chloride Injection, USP prior to intravenous infusion. Each single-use vial contains 100 mg of paclitaxel and approximately 900 mg of human albumin Each milliliter (mL) of reconstituted suspension contains 5 mg paclitaxel. ABRAXANE® is free of solvents.

While the technology disclosed in the U.S. Pat. No. 5,439,686 is highly useful for drug delivery, it produces amorphous nanoparticles of the substantially water-insoluble pharmaceutical agent alone suspended in a protein solution. Since there is no other stabilizing forces between molecules of the substantially water-insoluble agent in the amorphous particle state except weak van der Waals interactions between them, they are prone to instability such as Ostwald ripening, since the dissolution of the amorphous particles are determined mainly by the solubility of the compound in the amorphous particles in a given medium.

Indeed, when the method described in U.S. Pat. No. 5,439,686 to produce nanoparticle dispersion was applied to produce docetaxel nanoparticle dispersion, the particles began to precipitate within 1 hour of the preparation due to Ostwald ripening. Thus the method disclosed in U.S. Pat. Nos. 5,439,686 and 5,916,596 for producing nanoparticle dispersion is not useful for the preparation of certain substantially water-insoluble pharmaceutical agents such as docetaxel nanoparticles dispersed in aqueous medium and there is a need for a new process to make stable nanoparticle dispersion of substantially water-insoluble pharmaceutical agents in aqueous solution.

US patent application 20040247660 discloses compositions and methods for protein stabilized liposomes, the creation of protein stabilized liposomes, and the administration of protein stabilized liposomes. The process involves the use of oil-in water emulsion using protein as stabilizers for the preparation of liposomes using solvent evaporation technique and produces liposomes with different physical charactertics than the solid amorphous nanoparticles disclosed in the present invention.

US patent application 20050009908 discloses a process for the preparation of a stable dispersion of solid particles, in an aqueous medium comprising combining (a) a first solution comprising a substantially water-insoluble substance, a water-miscible organic solvent and an inhibitor with (b) an aqueous phase comprising water and optionally a stabiliser, thereby precipitating solid particles comprising the inhibitor and the substantially water-insoluble substance; and optionally removing the water-miscible organic solvent; wherein the inhibitor is a non-polymeric hydrophobic organic compound as defined in the description. The process provides a dispersion of solid particles in an aqueous medium, which particles exhibit reduced particle growth mediated by Ostwald ripening. The application describes the preparation of nanoparticles through precipitation technique using water miscible organic solvents. The problem with the method is to control the size of the particle as it is difficult to control the particle size through precipitation technique. This method is entirely different from the present invention wherein water immiscible organic solvent is used to form fine oil-in water emulsion and subsequent evaporation of water immiscible organic solvent to form nano-particles.

US application 20060141043A discloses the preparation of a stable dispersion of solid particles, in an aqueous medium comprising combining (a) a first solution comprising a substantially water-insoluble substance which is a thiazole compound, a water-miscible organic solvent and an inhibitor with (b) an aqueous phase comprising water and optionally a stabiliser, thereby precipitating solid particles comprising the inhibitor and the substantially water-insoluble substance; and optionally removing the water-miscible organic solvent; wherein the inhibitor is a non-polymeric hydrophobic organic compound.

Method for Nanoparticle Preparation:

There are several methods disclosed in the literature for the preparation of solid nanoparticles. For example, solid lipid nanoparticles (SLN) are nanoparticles with a matrix being composed of a solid lipid, i.e. the lipid is solid at room temperature and also at body temperature (Muller et al., 1995; Lucks and Muller, 1996; Muller et al., 2000; Mehnert and Mader, 2001). The lipid is melted approximately 5° C. above its melting point and the drug dissolved or dispersed in the melted lipid. Subsequently, the melt is dispersed in a hot surfactant solution by high speed stirring. The coarse emulsion obtained is homogenised in a high-pressure unit, typically at 500 bar and three homogenisation cycles. A hot oil-in-water nanoemulsion is obtained, cooled, the lipid recrystallises and forms solid lipid nanoparticles. Identical to the drug nanocrystals the SLN possess adhesive properties. They adhere to the gut wall and release the drug exactly where it should be absorbed. In addition the lipids are known to have absorption promoting properties, not only for lipophilic drugs such as Vitamin E but also drugs in general (Porter and Charman, 2001; Sek et al., 2001; Charman, 2000). There are even differences in the lipid absorption enhancement depending on the structure of the lipids (Sek et al., 2002). Basically, the body is taking up the lipid and the solubilised drug at the same time.

Meanwhile the second generation of lipid nanoparticles with solid matrix has been developed, the so-called nanostructured lipid carriers (Muller et al., 2000b). The NLC® are characterised that a certain nanostructure is given to their particle matrix by preparing the lipid matrix from a blend of a solid lipid with a liquid lipid (oil). The mixture is still solid at 40° C. These particles have improved properties regarding payload of drugs, more flexibility in modulating the drug release profile and being also suitable to trigger drug release (Muller et al., 2002; Radtke and Muller, 2001b). They can also be used for oral and parenteral drug administration identical to SLN, but have some additional interesting features.

In the LDC® nanoparticle technology (Muller and Olbrich, 1999b, 2000b, 2000c), the "conjugates" (term used in its broadest sense) were prepared either by salt formation (e.g. amino group containing molecule with fatty acid) or alternatively by covalent linkage (e.g. ether, ester, e.g. tributyrin). Most of the lipid conjugates melt somewhere about approximately 50-100° C. The conjugates are melted and dispersed in a hot surfactant solution. Further processing was performed identical to SLN and NLC. The obtained emulsion system is homogenised by high-pressure homogenisation, the obtained nanodispersion cooled, the conjugate recrystallises and forms LDC nanoparticles. One could consider this suspension also as a nanosuspension of a pro-drug.

U.S. Pat. No. 6,207,178 discloses the preparation of suspensions of colloidal solid lipid particles (SLPs) of predominantly anisometrical shape with the lipid matrix being in a stable polymorphic modification and of suspensions of micron and submicron particles of bioactive agents (PBAs). A suspension stable for at least about 12 months of particles of bioactive agents (PBAs) manufactured by an emulsifying process having the following steps: (a) melting at least one solid bioactive agent; (b) heating a dispersion medium to approximately the same temperature as said at least one molten solid bioactive agent formed by step (a); (c) adding at least one highly mobile water-soluble or dispersible stabilizer, which does not form a separate phase in the dispersion medium, to the dispersion medium in an amount effective after emulsification to stabilize newly created surfaces during recrystallization, and optionally adding at least one lipid-soluble or dispersible stabilizer to said at least one molten bioactive agent; (d) premixing said at least one molten bioactive agent and the dispersion medium, and subsequently homogenizing said mixture by high pressure homogenization, micro-fluidization and/or ultrasonication; and (e) allowing the homogenized dispersion to cool until solid particles are formed by recrystallization of the dispersed bioactive agents.

One of the problem of applying these techniques for the preparation of solid nanoparticles containing taxanes are the fact that some of the taxanes such as docetaxel are prone to decomposition at high temperatures as used in these techniques. Another disadvantage is the formation of crystalline nanoparticles which may affect the stability and release characteristics of the encapsulated drug.

Another common method for the preparation of solid nanoparticles is by the solvent evaporation of an oil-in-water emulsion. The oil-phase contains one or more pharmaceutical substances and the aqueous phase contains just the buffering materials or an emulsifier. An emulsion consists of two immiscible liquids (usually oil and water), with one of the liquids dispersed as small spherical droplets in the other. In most foods, for example, the diameters of the droplets usually lie somewhere between 0.1 and 100 μm (Dickinson and Stainsby 1982, Dickinson 1992). An emulsion can be conveniently classified according to the distribution of the oil and aqueous phases. A system that consists of oil droplets dispersed in an aqueous phase is called an oil-in-water or O/W emulsion (e.g, mayonnaise, milk, cream etc.). A system that consists of water droplets dispersed in an oil phase is called a water-in-oil or W/O emulsion (e.g. margarine, butter and spreads). The process of converting two separate immiscible liquids into an emulsion, or of reducing the size of the droplets in a preexisting emulsion, is known as homogenization.

It is possible to form an emulsion by homogenizing pure oil and pure water together, but the two phases rapidly separate into a system that consists of a layer of oil (lower density) on top of a layer of water (higher density). This is because droplets tend to merge with their neighbors, which eventually leads to complete phase separation. Emulsions usually are thermodynamically unstable systems. It is possible to form emulsions that are kinetically stable (metastable) for a reasonable period of time (a few minutes, hours, days, weeks, months, or years) by including substances known as emulsifiers and/or thickening agent prior to homogenization.

Emulsifiers are surface-active molecules that adsorb to the surface of freshly formed droplets during homogenization, forming a protective membrane that prevents the droplets from coming close enough together to aggregate. Most emulsifiers are molecules having polar and nonpolar regions in the same molecule. The most common emulsifiers used in the food industry are amphiphilic proteins, small-molecule surfactants, and monoglycerides, such as sucrose esters of fatty acids, citric acid esters of monodiglycerides, salts of fatty acids, etc (Krog, 1990).

Thickening agents are ingredients that are used to increase the viscosity of the continuous phase of emulsions and they enhance emulsion stability by retarding the movement of the droplets. A stabilizer is any ingredient that can be used to enhance the stability of an emulsion and may therefore be either an emulsifier or thickening agent.

The term "emulsion stability" is broadly used to describe the ability of an emulsion to resist changes in its properties with time. Emulsions may become unstable through a variety of physical processes including creaming, sedimentation, flocculation, coalescence, and phase inversion. Creaming and sedimentation are both forms of gravitational separation. Creaming describes the upward movement of droplets due to the fact that they have a lower density than the surrounding liquid, whereas sedimentation describes the downward movement of droplets due to the fact that they have a higher density than the surrounding liquid. Flocculation and coalescence are both types of droplet aggregation. Flocculation occurs when two or more droplets come together to form an aggregate in which the droplets retain their individual integrity, whereas coalescence is the process where two or more droplets merge together to form a single larger droplet. Extensive droplet coalescence can eventually lead to the formation of a separate layer of oil on top of a sample, which is known as "oiling off".

Most emulsions can conveniently be considered to consist of three regions that have different physicochemical properties: the interior of the droplets, the continuous phase, and the interface. The molecules in an emulsion distribute themselves among these three regions according to their concentration and polarity (Wedzicha 1988). Nonpolar molecules tend to be located primarily in the oil phase, polar molecules in the aqueous phase, and amphiphilic molecules at the interface. It should be noted that even at equilibrium, there is a continuous exchange of molecules between the different regions, which occurs at a rate that depends on the mass transport of the molecules through the system. Molecules may also move from one region to another when there is some alteration in the environmental conditions of an emulsion (e.g, a change in temperature or dilution within the mouth). The location and mass transport of the molecules within an emulsion have a significant influence on the aroma, flavor release, texture, and physicochemical stability of food products (Dickinson 1982; Wedzicha 1991; Coupland 1996).

Many properties of the emulsions can only be understood with reference to their dynamic nature. The formation of emulsions by homogenization is a highly dynamic process which involves the violent disruption of droplets and the rapid movement of surface-active molecules from the bulk liquids to the interfacial region. Even after their formation, the droplets in an emulsion are in continual motion and frequently collide with one another because of their Brownian motion, gravity, or applied mechanical forces (Melik 1988; Dukhin 1996). The continual movement and interactions of droplets cause the properties of emulsions to evolve over time due to the various destabilization processes such as change in temperature or in time.

The most important properties of emulsion are determined by the size of the droplets they contain (Dickinson 1982; 1992). Consequently, it is important to control, predict and measure, the size of the droplets in emulsions. If all the droplets in an emulsion are of the same size, the emulsion is referred to as monodisperse, but if there is a range of sizes present, the emulsion is referred to as polydisperse. The size of the droplets in a monodisperse emulsion can be completely characterized by a single number, such as the droplet diameter (d) or radius (r). Monodisperse emulsions are sometimes used for fundamental studies because the interpretation of experimental measurements is much simpler than that of polydisperse emulsions. Nevertheless, emulsions by homogenization always contain a distribution of droplet sizes, and so the specification of their droplet size is more complicated than that of monodisperse systems. Ideally, one would like to have information about the full particle size distribution of an emulsion (i.e, the size of each of the droplets in the system). In many situations, knowledge of the average size of the droplets and the width of the distribution is sufficient (Hunter 1986).

An efficient emulsifier produces an emulsion in which there is no visible separation of the oil and water phases over time. Phase separation may not become visible to the human eye for a long time, even though some emulsion breakdown has occurred. A more quantitative method of determining emulsifier efficiency is to measure the change in the particle size distribution of an emulsion with time. An efficient emulsifier produces emulsions in which the particle size distribution does not change over time, whereas a poor emulsifier produces emulsions in which the particle size increases due to coalescence and/or flocculation. The kinetics of emulsion stability can be established by measuring the rate at which the particle size increases with time.

Proteins as Emulsifiers:

In oil-in-water emulsions, proteins are used mostly as surface active agents and emulsifiers. One of the food proteins used in o/w emulsions is whey proteins. The whey proteins include four proteins: β-lactoglobulin, α-lactalbumin, bovine serum albumin and immunoglobulin (Tornberg 1990). Commercially, whey protein isolates (WPI) with isoelectric point ~5 (Tornberg 1990) are used for o/w emulsion preparation. According to Hunt (1995), whey protein concentrations of 8% have been used to produce self-supporting gels. Later on, the limiting concentrations of whey protein to produce self-supporting gels are known to be reduced to 4-5%. It is possible to produce gels at whey protein concentrations as low as 2% w/w, using heat treatments at 90° C. or 121° C. and ionic strength in excess of 50 mM (Hunt 1995).

U.S. Pat. No. 6,106,855 discloses a method for preparing stable oil-in-water emulsions by mixing oil, water and an insoluble protein at high shear. By varying the amount of insoluble protein the emulsions may be made liquid, semi-solid or solid. The preferred insoluble proteins are insoluble fibrous proteins such as collagen. The emulsions may be medicated with hydrophilic or hydrophobic pharmacologically active agents and are useful as or in wound dressings or ointments.

U.S. Pat. No. 6,616,917 discloses an invention relating to a transparent or translucent cosmetic emulsion comprising an aqueous phase, a fatty phase and a surfactant, the said fatty phase containing a miscible mixture of at least one cosmetic oil and of at least one volatile fluoro compound, the latter compound being present in a proportion such that the refractive index of the fatty phase is equal to ±0.05 of that of the aqueous phase. The invention also relates to the process for preparing the emulsion and the use of the emulsion in skincare, hair conditioning and antisun protection and/or artificial tanning.

Proteins derived from whey are widely used as emulsifiers (Phillips 1994; Dalgleish 1996). They adsorb to the surface of oil droplets during homogenization and form a protective membrane, which prevents droplets from coalescing (Dickinson 1998). The physicochemical properties of emulsions stabilized by whey protein isolates (WPI) are related to the aqueous phase composition (e.g, ionic strength and pH) and the processing and storage conditions of the product (e.g, heating, cooling, and mechanical agitation). Emulsions are prone to flocculation around the isoelectric point of the WPI, but are stable at higher or lower pH (Philips 1994). The stability to flocculation could be interpreted in terms of colloidal interactions between droplets, i.e, van der Waals, electrostatic repulsion and steric forces (Philips 1994; Dalgleish 1996). The van der Waals interactions are fairly short-range due to their dependence on the inverse 6th power of the distance. Electrostatic interactions between similarly charged droplets are repulsive, and their magnitude and range decrease with increasing ionic strength. Short range interactions become important at droplet separations of the order of the thickness of the interfacial layer or less, e.g, steric, thermal fluctuation and hydration forces (Israelachvili 1992). Such interactions are negligible at distances greater than the thickness of the interfacial layer, but become strongly repulsive when the layers overlap, preventing droplets from getting closer. It has been shown that the criteria for the protein emulsifiers appear to be the ability to adsorb quickly at the oil/water interface and surface hydrophobicity is of secondary importance (Lockhead 1999).

Thus, in the preparation of nanoparticle using solvent evaporation technique, proteins can be used as emulsifier to form the fine oil-in-water emulsion and subsequently the organic solvent in the emulsion can be evaporated to form the nanoparticles. Human serum albumin can be ideal for such preparations as it is non-immunogenic in humans, has the desired property as an emulsifier and has preferential targeting property to tumor sites. The measurements using the phosphorescence depolarization technique support a rather rigid heart shaped structure (8 nm×8 nm×3.2 nm) of albumin in neutral solution of BSA as in the crystal structure of human serum albumin (Ferrer 2001) and serum albumin has been shown to have good gelling properties (Hegg 1982).

Polymers as Emulsifiers:

Apart from proteins as emulsifiers, several natural, semi-natural and synthetic polymers can be used as emulsifiers. The polymer emulsifiers include naturally occurring emulsifiers, for example, agar, carageenan, furcellaran, tamarind seed polysaccharides, gum tare, gum karaya, pectin, xanthan gum, sodium alginate, tragacanth gum, guar gum, locust bean gum, pullulan, jellan gum, gum Arabic and various starches. Semisynthetic emulsifieres include carboxymethyl cellulose (CMC), methyl cellulose (MC), hydroxyethyl cellulose (HEC), alginic acid propylene glycol ester, chemically modified starches including soluble starches, and synthetic polymers including polyvinyl alcohol, polyethylene glycol and sodium polyacrylate. These polymer emulsifiers are used in the production of emulsion compositions such as emulsion flavors or powder compositions such as powder fats and oils and powder flavors. The powder composition is produced by emulsifying an oil, a lipophilic flavor or the like, and an aqueous component with a polymer emulsifier and then subjecting the emulsion to spray drying or the like. In this case, the powder composition is often in the form of a microcapsule.

Ostwald Ripening:

Generally, if particles with a wide range of sizes are dispersed in a medium there will be a differential rate of dissolution of the particles in the medium. The differential dissolution results in the smaller particles being thermodynamically unstable relative to the larger particles and gives rise to a flux of material from the smaller particles to the larger particles. The effect of this is that the smaller particles dissolve in the medium, whilst the dissolved material is deposited onto the larger particles thereby giving an increase in particle size. One such mechanism for particle growth is known as Ostwald ripening (Ostwald 1896 & 1897). Ostwald ripening has been studied extensively due to its importance in material and pharmaceutical sciences (Baldan 2002; Voorhees 1992; Madras 2001 & 2002; Lifshitz 1961 and Davies 1981).

The growth of particles in a dispersion can result in instability of the dispersion during storage resulting in the sedimentation of particles from the dispersion. It is particularly important that the particle size in a dispersion of a pharmacologically active compound remains constant because a change in particle size is likely to affect the bioavailability, toxicity and hence the efficacy of the compound. Furthermore, if the dispersion is required for intravenous administration, growth of the particles in the dispersion may render the dispersion unsuitable for this purpose, possibly leading to adverse or dangerous side effects.

Theoretically particle growth resulting from Ostwald ripening would be eliminated if all the particles in the dispersion were the same size. However, in practice, it is impossible to achieve a completely uniform particle size and even small differences in particle sizes can give rise to particle growth.

U.S. Pat. No. 4,826,689 describes a process for the preparation of uniform sized particles of a solid by infusing an aqueous precipitating liquid into a solution of the solid in an organic liquid under controlled conditions of temperature and infusion rate, thereby controlling the particle size. U.S. Pat. No. 4,997,454 describes a similar process in which the precipitating liquid is non-aqueous. However, when the particles have a small but finite solubility in the precipitating medium particle size growth is observed after the particles have been precipitated. To maintain a particular particle size using these processes it is necessary to isolate the particles as soon as they have been precipitated to minimise particle growth. Therefore, particles prepared according to these processes cannot be stored in a liquid medium as a dispersion. Furthermore, for some materials the rate of Ostwald ripening is so great that it is not practical to isolate small particles (especially nano-particles) from the suspension.

Higuchi and Misra (J. Pharm. Sci., 51 (1962) 459) describe a method for inhibiting the growth of the oil droplets in oil-in-water emulsions by adding a hydrophobic compound (such as hexadecane) to the oil phase of the emulsion. U.S. Pat. No. 6,074,986 (WO95/07614) describes the addition of a polymeric material having a molecular weight of up to 10,000 to the disperse oil phase of an oil-in-water emulsion to inhibit Ostwald ripening. Welin-Berger et al. (Int. Jour. of Pharmaceutics 200 (2000) pp 249-260) describe the addition of a hydrophobic material to the oil phase of an oil-in-water emulsion to inhibit Ostwald ripening of the oil droplets in the emulsion. In these latter three references the material added to the oil phase is dissolved in the oil phase to give a single phase oil dispersed in the aqueous continuous medium.

EP 589 838 describes the addition of a polymeric stabilizer to stabilize an oil-in-water emulsion wherein the disperse phase is a hydrophobic pesticide dissolved in a hydrophobic solvent.

U.S. Pat. No. 4,348,385 discloses a dispersion of a solid pesticide in an organic solvent to which is added an ionic dispersant to control Ostwald ripening.

WO 99/04766 describes a process for preparing vesicular nano-capsules by forming an oil-in-water emulsion wherein the dispersed oil phase comprises a material designed to form a nano-capsule envelope, an organic solvent and optionally an active ingredient. After formation of a stable emulsion the solvent is extracted to leave a dispersion of nano-capsules.

U.S. Pat. No. 5,100,591 describes a process in which particles comprising a complex between a water insoluble substance and a phospholipid are prepared by co-precipitation of the substance and phospholipid into an aqueous medium. Generally the molar ratio of phospholipid to substance is 1:1 to ensure that a complex is formed.

U.S. Pat. No. 4,610,868 describes lipid matrix carriers in which particles of a substance is dispersed in a lipid matrix. The major phase of the lipid matrix carrier comprises a hydrophobic lipid material such as a phospholipid.

There has been no recognition or appreciation in the art that prior to this application that a substantially stable nanoparticle by inhibiting the Ostwald ripening can be formed by the solvent evaporation of an oil-in-water emulsion using protein such as serum albumin or a polymer such as polyvinyl alcohol as emulsifying agent. The present invention discloses a new drug delivery system for the delivery of substantially water insoluble pharmaceutical substances selected as nanoparticles without appreciable Ostwald ripening effect for the treatment of diseases in humans with reduced toxicity.

DISCLOSURE OF THE INVENTION

We have surprisingly found that substantially stable dispersions of solid particles of docetaxel in an aqueous medium can be prepared using an oil-in-water emulsuion process using protein or other polymer as a surfactant. The dispersions prepared according to the present invention exhibit little or no particle growth after the formation mediated by Ostwald ripening.

According to a first aspect of the present invention there is provided a process for the preparation of a substantially stable dispersion of solid particles in an aqueous medium comprising:

combining (a) a first solution comprising a substantially water-insoluble substance, a water-immiscible organic solvent, optionally a water-miscible organic solvent and an Ostwald ripening inhibitor with (b) an aqueous phase comprising water and an emulsifier, preferabley a protein; forming an oil-in-water emulsion under high pressure homogenization and rapidly evaporating the water immiscible solvent under vacuum thereby producing solid particles comprising the Ostwald ripening inhibitor and the substantially water-insoluble substance;

wherein:
(i) the Ostwald ripening inhibitor is a non-polymeric hydrophobic organic compound that is substantially insoluble in water;

(ii) the Ostwald ripening inhibitor is less soluble in water than the substantially water-insoluble substance; and
(iii) the Ostwald ripening inhibitor is not a phospholipid.

The process according to the present invention enables substantially stable dispersions of very small particles, especially nano-particles, to be prepared in high concentration without the particle growth.

The dispersion according to the present invention is substantially stable, by which we mean that the solid particles in the dispersion exhibit reduced or substantially no particle growth mediated by Ostwald ripening. By the term "reduced particle growth" is meant that the rate of particle growth mediated by Ostwald ripening is reduced compared to particles prepared without the use of an Ostwald ripening inhibitor. By the term "substantialy no particle growth" is meant that the mean particle size of the particles in the aqueous medium does not increase by more than 10% (more preferably by not more than 5%) over a period of 12-120 hours at 20° C. after the dipersion into the aqueous phase in the present process. By the term "substantially stable particle or nano-particle" is meant that the mean particle size of the particles in the aqueous medium does not increase by more than 10% (more preferably by not more than 5%) over a period of 12-120 hours at 20° C. Preferably the particles exhibit substantially no particle growth over a period of 12-120 hours, more preferably over a period 24-120 hours and more preferably 48-120 hours.

It is to be understood that in those cases where the solid particles are prepared in an amorphous form the resulting particles will, generally, eventually revert to a thermodynamically more stable crystalline form upon storage as an aqueous dispersion. The time taken for such dispersions to re-crystallise is dependent upon the substance and may vary from a few hours to a number of days. Generally such re-crystallisation will result in particle growth and the formation of large crystalline particles which are prone to sedimentation from the dispersion. It is to be understood that the present invention does not prevent conversion of amorphous particles in the suspension into a crystalline state. The presence of the Ostwald ripening inhibitor in the particles according to the present invention significantly reduces or eliminates particle growth mediated by Ostwald ripening, as hereinbefore described. The particles are therefore stable to Ostwald ripening and the term "stable" used herein is to be construed accordingly.

The solid particles in the dispersion preferably have a mean particle size of less than 10 μm, more preferably less than 5 μm, still more preferably less than 1 μm and especially less than 500 nm. It is especially preferred that the particles in the dispersion have a mean particle size of from 10 to 500 nm, more especially from 50 to 300 nm and still more especially from 50 to 200 nm. The mean size of the particles in the dispersion may be measured using conventional techniques, for example by dynamic light scattering to measure the intensity-averaged particle size.

Generally the solid particles in the dispersion prepared according to the present invention exhibit a narrow unimodal particle size distribution.

The solid particles may be crystalline, semi-crystalline or amorphous. In an embodiment, the solid particles comprise a pharmacologically active substance in a substantially amorphous form. This can be advantageous as many pharmacological compounds exhibit increased bioavailability in amorphous form compared to their crystalline or semi-crystalline forms. The precise form of the particles obtained will depend upon the conditions used during the evaporation step of the process. Generally, the present process results in rapid evaporation of the emulsion and the formation of substantially amorphous particles.

This invention provides a method for producing solid nanoparticles with mean diameter size of less than 220 nm, more preferably with a mean diameter size of about 20-200 nm and most preferably with a mean diameter size of about 50-180 nm. These solid nanoparticle suspensions can be sterile filtered through a 0.22 μm filter and lyophilized. The sterile suspensions can be lyophilized in the form of a cake in vials with or without cryoprotectants such as sucrose, mannitol, trehalose or the like. The lyophilized cake can be reconstituted to the original solid nanoparticle suspensions, without modifying the nanoparticle size, stability and the drug potency, and the cake is stable for more than 24 months.

In another embodiment, the sterile-filtered solid nanoparticles can be lyophilized in the form of a cake in vials using cryoprotectants such as sucrose, mannitol, trehalose or the like. The lyophized cake can be reconstituted to the original liposomes, without modifying the particle size of solid nanoparticles. These nanoparticles are administered by a variety of routes, preferably by intravenous, parenteral, intratumoral and oral routes.

BRIEF DESCRIPTION OF THE DRAWINGS

In the drawings, like elements are depicted by like reference numerals. The drawings are briefly described as follows. The accompanying drawings, which are incorporated in and form part of the specification, illustrate the embodiments of the present invention and, together with the description, serve to explain the principles of the invention.

FIG. 1 is a picture of the chemical structure of taxanes.

FIG. 2 is a picture of tubulin-microtubule dynamics (Kingston 2001).

FIG. 3 is a picture of the chemical structure of epothilone.

FIG. 4 is a graph of the particle size analysis of 4% albumin after homogenization with chloroform and ethanol.

FIG. 5 is a graph of the particle size analysis of 4% albumin.

FIG. 6 is six graphs (A to F) of the particle size analysis of docetaxel containing cholesterol as inhibitor. FIG. 6(A) shows the particle size analysis of docetaxel containing cholesterol as inhibitor after reconstitution. FIG. 6(B) shows the particle size analysis of docetaxel containing cholesterol as inhibitor after 2 hours kept at 24° C. FIG. 6(C) shows the particle size analysis of docetaxel containing cholesterol as inhibitor after 3 hours kept at 24° C. FIG. 6(D) shows the particle size analysis of docetaxel containing cholesterol as inhibitor after 5 hours kept at 24° C. FIG. 6(E) shows the particle size analysis of docetaxel containing cholesterol as inhibitor after 2 hours kept at 2-6° C. FIG. 6(F) shows the particle size analysis of docetaxel containing cholesterol as inhibitor after 5 hours kept at 2-5° C.

FIG. 7 is five graphs (A to E) of the particle size analysis of docetaxel containing cholesteryl stearate and cholesterol as inhibitors. FIG. 7(A) shows particle size analysis of docetaxel containing cholesteryl stearate and cholesterol as inhibitors after reconstitution. FIG. 7(B) shows particle size analysis of docetaxel containing cholesteryl stearate and cholesterol as inhibitors after 40 hours kept at 24° C. FIG. 7(C) shows particle size analysis of docetaxel containing cholesteryl stearate and cholesterol as inhibitors after 40 hours kept at 2-6° C. FIG. 7(D) shows particle size analysis of docetaxel containing cholesteryl stearate and cholesterol as inhibitors after 4 days kept at 24° C. FIG. 7(E) shows particle size analysis of docetaxel containing cholesteryl stearate and cholesterol as inhibitors after 40 hours kept at 24° C.

FIG. 8 is eight graphs (A to H) of the particle size analysis of docetaxel containing hexadecyldexadecanoate and cholesterol as inhibitors. FIG. 8(A) shows particle size analysis of docetaxel containing hexadecyldexadecanoate and cholesterol as inhibitors after reconstitution. FIG. 8(B) shows particle size analysis of docetaxel containing hexadecyldexadecanoate and cholesterol as inhibitors after 1 hour kept at 24° C. FIG. 8(C) shows particle size analysis of docetaxel containing hexadecyldexadecanoate and cholesterol as inhibitors after 20 hours kept at 24° C. FIG. 8(D) shows particle size analysis of docetaxel containing hexadecyldexadecanoate and cholesterol as inhibitors after 20 hours kept at 2-6° C. FIG. 8(E) shows particle size analysis of docetaxel containing hexadecyldexadecanoate and cholesterol as inhibitors after 3 days kept at 24° C. FIG. 8(F) shows particle size analysis of docetaxel containing hexadecyldexadecanoate and cholesterol as inhibitors after 3 days kept at 2-6° C. FIG. 8(G) shows particle size analysis of docetaxel containing hexadecyldexadecanoate and cholesterol as inhibitors after 5 days kept at 24° C. FIG. 8(H) shows particle size analysis of docetaxel containing hexadecyldexadecanoate and cholesterol as inhibitors after 5 days kept at 2-6° C.

FIG. 9 is eight graphs (A to H) of the particle size analysis of docetaxel containing glyceryl tristearate and cholesterol as inhibitors. FIG. 9(A) shows the particle size analysis of docetaxel containing glyceryl tristearate and cholesterol as inhibitors after reconstitution. FIG. 9(B) shows the particle size analysis of docetaxel containing glyceryl tristearate and cholesterol as inhibitors after 1 hour kept at 24° C. FIG. 9(C) shows the particle size analysis of docetaxel containing glyceryl tristearate and cholesterol as inhibitors after 20 hours kept at 24° C. FIG. 9(D) shows the particle size analysis of docetaxel containing glyceryl tristearate and cholesterol as inhibitors after 20 hours kept at 2-6° C. FIG. 9(E) shows the particle size analysis of docetaxel containing glyceryl tristearate and cholesterol as inhibitors after 3 days kept at 24° C. FIG. 9(F) shows the particle size analysis of docetaxel containing glyceryl tristearate and cholesterol as inhibitors after 3 days kept at 2-6° C. FIG. 9(G) shows the particle size analysis of docetaxel containing glyceryl tristearate and cholesterol as inhibitors after 5 days kept at 24° C. FIG. 9(H) shows the particle size analysis of docetaxel containing glyceryl tristearate and cholesterol as inhibitors after 5 days kept at 2-6° C.

FIG. 10 shows graphs (A and B) of the particle size analysis of docetaxel without any inhibitors. FIG. 10(A) shows the particle size analysis of docetaxel without any inhibitors after reconstitution. FIG. 10(B) shows the particle size analysis of docetaxel without any inhibitors after 1 hour kept at 24° C.

FIG. 11 (graphs A-I) shows particle sizs compared during the process of evaporation of the organic solvent. FIG. 11(A) shows particle size immediately after the evaporation of the organic solvent. FIG. 11(B) shows after 30 mins kept at 24° C. FIG. 11(C) shows after 60 mins kept at 24° C. FIG. 11(D) shows after 90 mins at 24° C. FIG. 11(E) shows after 120 mins at 24° C. FIG. 11(F) shows after 30 mins at 5° C. FIG. 11(G) shows after 60 mins at 5° C. FIG. 11(H) shows after 90 mins kept at 5° C. FIG. 11(I) shows after 120 mins kept at 5° C.

BEST MODE FOR CARRYING OUT THE INVENTION

It is understood as "microtubule inhibitor" the ability to interfere with microtubule dynamics or stability to inhibit cell division and lead to cell death. Such an action is performed by several natural, semisynthetic and synthetic compounds. They are classified by their binding sites on tubulin. There are three general classes of drug binding sites on tubulin, the colchicine binding site, the taxol site and the *vinca* alkaloid site. Most other drugs appear to bind in competitive or noncompetitive fashion with at least one of these drugs, suggesting they share overlapping binding motifs. There are also three general modes of interaction, tubulin-sequestering drugs like colchicine, drugs that induce alternate polymers like *vinca* alkaloids, and drugs that stabilize microtubules like taxol. The term "microtubule inhibitor" is often used as a generic word for all compounds that bind to tubulin and interfere with microtubule dynamics; similarly, the receptor for these compounds is generally known as "tubulin". Microtubule inhibitors are also called as tubulin inhibitors, anti-tubulin agents, mitotic inhibitors, anti-microtubule agents and anti-mitotic agents.

As used herein, the term "μm" or the term "micrometer or micron" refers to a unit of measure of one one-millionth of a meter.

As used herein, the term "nm" or the term "nanometer" refers to a unit of measure of one one-billionth of a meter.

As used herein, the term "μg" or the term "microgram" refers to a unit of measure of one one-millionth of a gram.

As used herein, the term "ng" or the term "nanogram" refers to a unit of measure of one one-billionth of a gram.

As used herein, the term "mL" refers to a unit of measure of one one-thousandth of a liter.

As used herein, the term "mM" refers to a unit of measure of one one-thousandth of a mole.

As used herein, the term "biocompatible" describes a substance that does not appreciably alter or affect in any adverse way, the biological system into which it is introduced.

As used herein, the term "substantially water insoluble pharmaceutical substance or agent" means biologically active chemical compounds which are poorly soluble or almost insoluble in water. Examples of such compounds are paclitaxel, docetaxel, SN-38, oleandrin, cyclosporine, digitoxin and the like.

By the term "reduced particle growth" is meant that the rate of particle growth mediated by Ostwald ripening is reduced compared to particles prepared without the use of an Ostwald ripening inhibitor.

By the term "substantialy no particle growth" is meant that the mean particle size of the particles in the aqueous medium does not increase by more than 10% (more preferably by not more than 5%) over a period of 12-120 hours at 20° C. after the dipersion into the aqueous phase in the present process.

By the term "substantially stable particle or nano-particle" is meant that the mean particle size of the particles in the aqueous medium does not increase by more than 10% (more preferably by not more than 5%) over a period of 12-120 hours at 20° C. Preferably the particles exhibit substantially no particle growth over a period of 12-120 hours, more preferably over a period 24-120 hours and more preferably 48-120 hours.

The term "cell-proliferative diseases" is meant here to denote malignant as well as non-malignant cell populations which often appear morphologically to differ from the surrounding tissue.

The term "taxanes", as used herein, refers to the class of antineoplastic agents or anti-mitotic agents having a mechanism of microtubule action and having a structure which includes the unusual taxane ring system (see FIG. 1) and a stereospecific side chain that is required for cytostatic activity. Paclitaxel (also known as taxol), is the first clinically used taxane. Docetaxel, an active analog also in clinical use, is synthesized from 10-DAB III (U.S. Pat. No. 4,814,470, issued Mar. 21, 1989 to Colin et al.). A taxane designated SB-T-1011 has been synthesized from 14β-hydroxy-10-DAB III, also obtained from yew needles (Ojima et al. 1994). The side chain of paclitaxel contains two aromatic rings connected by an amide bond (FIG. 1), but the existence of other active analogs such as docetaxel (Gueritte-Voegelein et al. 1990; Gueritte-Voegelein et al. 1991) demonstrates that certain structural modifications to the basic paclitaxel side chain motif can be tolerated.

Examples of taxanes which may be used include but are not limited to taxol (paclitaxel); taxotere (docetaxel); MAC-321; TL-909; TL-310; spicatin; taxane-2, 13-dione, 5β, 9β, 10β-trihydroxy-, cyclic 9, 10-acetal with acetone, acetate; taxane-2, 13-dione, 5β, 9β, 10β-trihydroxy-, cyclic 9, 10-acetal with acetone; taxane-2β, 5β, 9β, 10β-tetrol, cyclic 9, 10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3'-phenylpropionyl)baccatin III; yunnanxol; 7-(4-Azidobenzoyl) baccatin III; N-debenzoyltaxol A; O-acetylbaccatin IV; 7-(triethylsilyl)baccatin III; 7, 10-Di-O-[(2,2,2-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deacetyl-7-epitaxol; epitaxol; 10-deacetyl-taxol C; 7-xylosyl-10-deacetyltaxol; 10-deacetyltaxol-7-xyloside; 7-epi-10-deacetyltaxol; 10-deacetyltaxol; and 10-deacetyltaxol B.

The term "docetaxel" refers to the active ingredient of TAXOTERE® or else TAXOTERE® itself.

The term "Ostwald ripening" refers to coarsening of a precipitate or solid particle dispersed in a medium and is the final stage of phase separation in a solution, during which the larger particles of the precipitate or the solid particle grow at the expense of the smaller particles, which disappear. As recognized by Ostwald (1896 & 1897), the driving force for the process which now bears his name is the increased solubility of the smaller particles due to surface tension between the precipitate or the solid particle and the solute. If one assumes that the solute is in local equilibrium with the precipitate or the solid particle, then this solubility difference induces a solute concentration gradient and leads to a diffusive flux from the smaller to the larger particles. One speaks of diffusion-controlled growth (as opposed to growth controlled by slow deposition of solute atoms at the particle surfaces).

The term "Inhibitor" refers in general to the organic substances which are added to the substantially water insoluble substance in order to reduce the instability of the solid nanoparticles dispersed in an aqueous medium due to Ostwald ripening.

In the preferred embodiment, the present invention provides solid nanoparticle formulations without particle growth due to Ostwald ripening of substantially water insoluble pharmaceutical substances selected from microtubule inhibitors and methods of preparing and employing such formulations.

The advantages of these nanoparticle formulations are that a substantially water insoluble pharmaceutical substance is co-precipitated with inhibitors of Ostwald ripening. These compositions have been observed to provide a very low toxicity form of the pharmacologically active agent that can be delivered in the form of nanoparticles or suspensions by slow infusions or by bolus injection or by other parenteral or oral delivery routes. These nanoparticles have sizes below 400 nm, preferably below 200 nm, and more preferably below 140 nm having hydrophilic proteins adsorbed onto the surface of the nanoparticles. These nanoparticles can assume different morphology; they can exist as amorphous particles or as crystalline particles.

By substantially insoluble is meant a substance that has a solubility in water at 25° C. of less than 0.5 mg/ml, preferably less than 0.1 mg/ml and especially less than 0.05 mg/ml.

The greatest effect on particle growth inhibition is observed when the substance has a solubility in water at 25° C. of more than 0.05 µg/ml. In a preferred embodiment the substance has a solubility in the range of from 0.05 µg/ml to 0.5 mg/ml, for example from 0.05 µg/ml to 0.05 mg/ml.

The solubility of the substance in water may be measured using a conventional technique. For example, a saturated solution of the substance is prepared by adding an excess amount of the substance to water at 25° C. and allowing the solution to equilibrate for 48 hours. Excess solids are removed by centrifugation or filtration and the concentration of the substance in water is determined by a suitable analytical technique such as HPLC.

The process according to the present invention may be used to prepare stable aqueous dispersions of a wide range of substantially water-insoluble substances. Suitable substances include but are not limited to pigments, pesticides, herbicides, fungicides, industrial biocides, cosmetics, pharmacologically active compounds and pharmacologically inert substances such as pharmaceutically acceptable carriers and diluents.

In a preferred embodiment the substantially water-insoluble substance is a substantially water-insoluble pharmacologically active substance. Numerous classes of pharmacologically active compounds are suitable for use in the present invention including but not limited to substantially water-insoluble anti-cancer agents (for example bicalutamide), steroids, preferably glucocorticosteroids (especially anti-inflammatory glucocorticosteroids, for example budesonide) antihypertensive agents (for example felodipine or prazosin), beta-blockers (for example pindolol or propranolol), hypolipidaemic agents, aniticoagulants, antithrombotics, antifungal agents (for example griseofluvin), antiviral agents, antibiotics, antibacterial agents (for example ciprofloxacin), antipsychotic agents, antidepressants, sedatives, anaesthetics, anti-inflammatory agents (including compounds for the treatment of gastrointestinal inflammatory diseases, for example compounds described in WO99/55706 and other anti-inflammatory compounds, for example ketoprofen), antihistamines, hormones (for example testosterone), immunomodifiers, or contraceptive agents. The substance may comprise a single substantially water-insoluble substance or a combination of two or more such substances.

Since the nanoparticle produced by the present invention are approximately 60-190 nm in diameters, they will have a reduced uptake by the RES, and, consequently, show a longer circulation time, increased biological and chemical stability, and increased accumulation in tumor-sites. Most importantly, the nanoparticle formulations can produce a marked enhancement of anti-tumor activity in mice against with substantial reduction in toxicity as the nanoparticles can alter the pharmacokinetics and biodistribution. This can reduce toxic side effects and increase efficacy of the therapy.
Ostwald Ripening Inhibitor:

The Ostwald ripening inhibitor is a non-polymeric hydrophobic organic compound that is less soluble in water than the substantially water-insoluble substance present in the water immiscible oragnic phase, and wherein the Ostwald ripening inhibitor is not a phospholipid. Suitable Ostwald ripening inhibitors have a water solubility at 25° C. of less than 0.1 mg/l, more preferably less than 0.01 mg/l. In an embodiment of the invention the Ostwald ripening inhibitor has a solubility in water at 25° C. of less than 0.05 µg/ml, for example from 0.1 ng/ml to 0.05 µg/ml.

In an embodiment of the invention the Ostwald ripening inhibitor has a molecular weight of less than 2000, such as less than 500, for example less than 400. In another embodiment of the invention the Ostwald ripening inhibitor has a molecular weight of less than 1000, for example less than 600. For example, the Ostwald ripening inhibitor may have a molecular weight in the range of from 200 to 2000, preferably a molecular weight in the range of from 400 to 1000, more preferably from 200 to 600.

Suitable Ostwald ripening inhibitors include an inhibitor selected from classes (i) to (vii) or a combination of two or more such inhibitors:

(i) a mono-, di- or (more preferably) a tri-glyceride of a fatty acid. Suitable fatty acids include medium chain fatty acids containing from 8 to 12, more preferably from 8 to 10 carbon atoms or long chain fatty acids containing more than 12 carbon atoms, for example from 14 to 20 carbon atoms, more preferably from 14 to 18 carbon atoms. The fatty acid may be saturated, unsaturated or a mixture of saturated and unsaturated acids. The fatty acid may optionally contain one or more hydroxyl groups, for example ricinoleic acid. The glyceride may be prepared by well known techniques, for example, esterifying glycerol with one or more long or medium chain fatty acids. In a preferred embodiment the Ostwald ripening inhibitor is a mixture of triglycerides obtainable by esterifying glycerol with a mixture of long or, preferably, medium chain fatty acids. Mixtures of fatty acids may be obtained by extraction from natural products, for example from a natural oil such as palm oil. Fatty acids extracted from palm oil contain approximately 50 to 80% by weight decanoic acid and from 20 to 50% by weight of octanoic acid. The use of a mixture of fatty acids to esterify glycerol gives a mixture of glycerides containing a mixture of different acyl chain lengths. Long and medium chain triglycerides are commercially available. For example a medium chain triglyceride (MCT) containing acyl groups with 8 to 12, more preferably 8 to 10 carbon atoms is prepared by esterification of glycerol with fatty acids extracted from palm oil, giving a mixture of triglycerides containing acyl groups with 8 to 12, more preferably 8 to 10 carbon atoms. This MCT is commercially available as Miglyol 812N (Huls, Germany) Other commercially available MCT's include Miglyol 810 and Miglyol 818 (Huls, Germany). A further suitable medium chain triglyceride is trilaurine (glycerol trilaurate). Commercially available long chain trigylcerides include glyceryl tri-stearate, glyceryl tri-palmitate, soya bean oil, sesame oil, sunflower oil, castor oil or rape-seed oil.

Mono and di-glycerides may be obtained by partial esterification of glycerol with a suitable fatty acid, or mixture of fatty acids. If necessary the mono- and di-glycerides may be separated and purified using conventional techniques, for example by extraction from a reaction mixture following esterification. When a mono-glyceride is used it is preferably a long-chain mono glyceride, for example a mono glyceride formed by esterification of glycerol with a fatty acid containing 18 carbon atoms;

(ii) a fatty acid mono- or (preferably) di-ester of a $C_{2-10}$ diol. Preferably the diol is an aliphatic diol which may be saturated or unsaturated, for example a $C_{2-10}$-alkane diol which may be a straight chain or branched chain diol. More preferably the diol is a $C_{2-6}$-alkane diol which may be a straight chain or branched chain, for example ethylene glycol or propylene glycol. Suitable fatty acids include medium and long chain fatty acids described above in relation to the glycerides. Preferred esters are di-esters of propylene glycol with one or more fatty acids containing from 10 to 18 carbon atoms, for example Miglyol 840 (Huls, Germany);

(iii) a fatty acid ester of an alkanol or a cycloalkanol. Suitable alkanols include $C_{1-20}$-alkanols which may be straight chain or branched chain, for example ethanol, propanol, isopropanol, n-butanol, sec-butanol or tert-butanol. Suitable cycloalkanols include $C_{3-6}$-cycloalkanols, for example cyclohexanol. Suitable fatty acids include medium and long chain fatty acids described above in relation to the glycerides. Preferred esters are esters of a $C_{2-6}$-alkanol with one or more fatty acids containing from 8 to 10 carbon atoms, or more preferably 12 to 29 carbon atoms, which fatty acid may saturated or unsaturated. Suitable esters include, for example dodecyl dodecanoate or ethyl oleate;

(iv) a wax. Suitable waxes include esters of a long chain fatty acid with an alcohol containing at least 12 carbon atoms. The alcohol may an aliphatic alcohol, an aromatic alcohol, an alcohol containing aliphatic and aromatic groups or a mixture of two or more such alcohols. When the alcohol is an aliphatic alcohol it may be saturated or unsaturated. The aliphatic alcohol may be straight chain, branched chain or cyclic. Suitable aliphatic alcohols include those containing more than 12 carbon atoms, preferably more than 14 carbon atoms especially more than 18 carbon atoms, for example from 12 to 40, more preferably 14 to 36 and especially from 18 to 34 carbon atoms. Suitable long chain fatty acids include those described above in relation to the glycerides, preferably those containing more than 14 carbon atoms especially more than 18 carbon atoms, for example from 14 to 40, more preferably 14 to 36 and especially from 18 to 34 carbon atoms. The wax may be a natural wax, for example bees wax, a wax derived from plant material, or a synthetic wax prepared by esterification of a fatty acid and a long chain alcohol. Other suitable waxes include petroleum waxes such as a paraffin wax;

(v) a long chain aliphatic alcohol. Suitable alcohols include those with 6 or more carbon atoms, more preferably 8 or more carbon atoms, such as 12 or more carbon atoms, for example from 12 to 30, for example from 14 to 28 carbon atoms. It is especially preferred that the long chain aliphatic alcohol has from 10 to 28, more especially from 14 to 22 carbon atoms, for example from 14 to 22 carbon atoms. The alcohol may be straight chain, branched chain, saturated or unsaturated. Examples of suitable long chain alcohols include, 1-hexadecanol, 1-octadecanol, or 1-heptadecanol; or (vi) a hydrogenated vegetable oil, for example hydrogenated castor oil;

(vii) cholesterol and fatty acid esters of cholesterol.

In one embodiment of the present invention the Ostwald ripening inhibitor is selected from a long chain triglyceride and a long chain aliphatic alcohol containing from 6 to 22, preferably from 10 to 20 carbon atoms. Preferred long chain triglycerides and long chain aliphatic alcohols are as defined above. In a preferred embodiment the Ostwald ripening inhibitor is selected from a long chain triglyceride containing acyl groups with from 12 to 18 carbon atoms or a mixture of such triglycerides and an ester aliphatic alcohol containing from 10 to 22 carbon atoms (preferably 1-hexadecanol) or a mixture thereof (for example hexadecyl hexadecanoate).

In another embodiment of the present invention the Ostwald ripening inhibitor is selected from an ester of cholesterol and cholesterol. Preferred cholesteryl ester is cholesteryl palmitate or stearate.

When the substantially water-insoluble substance is a pharmacologically active compound the Ostwald ripening inhibitor is preferably a pharmaceutically inert material.

The Ostwald ripening inhibitor is present in the particles in a quantity sufficient to prevent Ostwald ripening of the particles in the suspension. Preferably the Ostwald ripening inhibitor will be the minor component in the solid particles formed in the present process comprising the Ostwald ripening inhibitor and the substantially water-insoluble substance. Preferably, therefore, the Ostwald ripening inhibitor is present in a quantity that is just sufficient to prevent Ostwald ripening of the particles in the dispersion, thereby minimising the amount of Ostwald ripening inhibitor present in the particles.

In embodiments of the present invention the weight fraction of Ostwald ripening inhibitor relative to the total weight of Ostwald ripening inhibitor and substantially water-insoluble substance (i.e. weight of Ostwald ripening inhibitor/(weight of Ostwald ripening inhibitor+weight of substantially water-insoluble substance)) is from 0.01 to 0.99, preferably from 0.05 to 0.95, especially from 0.2 to 0.95 and more especially from 0.3 to 0.95. In a preferred embodiment the weight fraction of Ostwald ripening inhibitor relative to the total weight of Ostwald ripening inhibitor and substantially water-insoluble substance is less than 0.95, more preferably 0.9 or less, for example from 0.2 to 0.9, such as from 0.3 to 0.9, for example about 0.8. This is particularly preferred when the substantially water-insoluble substance is a pharmacologically active substance and the Ostwald ripening inhibitor is relatively non-toxic (e.g. a weight fraction above 0.8) which may not give rise to unwanted side effects and/or affect the dissolution rate/bioavailability of the pharmacologically active substance when administered in vivo.

Furthermore, we have found that in general a low weight ratio of Ostwald ripening inhibitor to the Ostwald ripening inhibitor and the substantially water-insoluble substance (i.e. less than 0.5) is sufficient to prevent particle growth by Ostwald ripening, thereby allowing small (preferably less than 1000 nm, preferably less than 500 nm) stable particles to be prepared. A small and constant particle size is often desirable, especially when the substantially water-insoluble substance is a pharmacologically active material that is used, for example, for intravenous administration.

One application of the dispersions prepared by the process according to the present invention is the study of the toxicology of a pharmacologically active compound. The dispersions prepared according to the present process can exhibit improved bioavailability compared to dispersions prepared using alternative processes, particularly when the particle size of the substance is less than 500 nm. In this application it is advantageous to minimise the amount of Ostwald ripening inhibitor relative to the active compound so that any effects on the toxicology associated with the presence of the Ostwald ripening inhibitor are minimised.

When the substantially water-insoluble substance has an appreciable solubility in the Ostwald ripening inhibitor the weight ratio of Ostwald ripening inhibitor to substantially water-insoluble substance should be selected to ensure that the amount of substantially water-insoluble substance exceeds that required to form a saturated solution of the substantially water-insoluble substance in the Ostwald ripening inhibitor. This ensures that solid particles of the substantially water-insoluble substance are formed in the dispersion. This is important when the Ostwald ripening inhibitor is a liquid at the temperature at which the dispersion is prepared (for example ambient temperature) to ensure that the process does not result in the formation liquid droplets comprising a solution of the substantially water-insoluble substance in the Ostwald ripening inhibitor, or a two phase system comprising the solid substance and large regions of the liquid Ostwald ripening inhibitor.

Without wishing to be bound by theory we believe that systems in which there is a phase separation between the substance and Ostwald ripening inhibitor in the particles are more prone to Ostwald ripening than those in which the solid particles form a substantially single phase system. Accordingly, in a preferred embodiment the Ostwald ripening inhibitor is sufficiently miscible in the substantially water-insoluble material to form solid particles in the dispersion comprising a substantially single-phase mixture of the substance and the Ostwald ripening inhibitor. The composition of the particles formed according to the present invention may be analysed using conventional techniques, for example analysis of the (thermodynamic) solubility of the substantially water-insoluble substance in the Ostwald ripening inhibitor, melting entropy and melting points obtained using routine differential scanning calorimetry (DSC) techniques to thereby detect phase separation in the solid particles. Furthermore, studies of nano-suspensions using nuclear magnetic resonance (NMR) (e.g. line broadening of either component in the particles) may be used to detect phase separation in the particles.

Generally the Ostwald ripening inhibitor should have a sufficient miscibility with the substance to form a substantially single phase particle, by which is meant that the Ostwald ripening inhibitor is molecularly dispersed in the solid particle or is present in small domains of Ostwald ripening inhibitor dispersed throughout the solid particle. It is thought that for many substances the substance/Ostwald ripening inhibitor mixture is a non-ideal mixture by which is meant that the mixing of two components is accompanied by a non-zero enthalpy change.

Preparation of the Inventive Nanoparticles:

In order to form the solid nanoparticles dispersed in an aqueous medium, substantially water insoluble pharmaceutical substance and the Ostwald ripening inhibitor(s) are dissolved in a suitable solvent (e.g., chloroform, methylene chloride, ethyl acetate, ethanol, tetrahydrofuran, dioxane, acetonitrile, acetone, dimethyl sulfoxide, dimethyl formamide, methyl pyrrolidinone, or the like, as well as mixtures of any two or more thereof). Additional solvents contemplated for use in the practice of the present invention include soybean oil, coconut oil, olive oil, safflower oil, cotton seed oil, sesame oil, orange oil, limonene oil, $C_1$-$C_{20}$ alcohols, $C_2$-$C_{20}$ esters, $C_3$-$C_{20}$ ketones, polyethylene glycols, aliphatic hydrocarbons, aromatic hydrocarbons, halogenated hydrocarbons and combinations thereof.

In the next stage, in order to make the solid nanoparticles, a protein (e.g., human serum albumin) is added (into the aqueous phase) to act as a stabilizing agent or an emulsifier for the formation of stable nanodroplets. Protein is added at a concentration in the range of about 0.05 to 25% (w/v), more preferably in the range of about 0.5%-10% (w/v).

In the next stage, in order to make the solid nanoparticles, an emulsion is formed by homogenization under high pressure and high shear forces. Such homogenization is conveniently carried out in a high pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent containing the substantially water insoluble pharmaceutical substance, the Ostwald ripening inhibitor and other agents. Acceptable methods of homogenization include processes imparting high shear and cavitation such as high pressure homogenization, high shear mixers, sonication, high shear impellers, and the like.

Finally, in order to make the solid nanoparticles, the solvent is evaporated under reduced pressure to yield a colloidal system composed of solid nanoparticles of substantially water insoluble pharmaceutical substance and the Ostwald ripening inhibitor(s) in solid form and protein. Acceptable methods of evaporation include the use of rotary evaporators, falling film evaporators, spray driers, freeze driers, and the like. Following evaporation of solvent, the liquid suspension may be dried to obtain a powder containing the pharmacologically active agent and protein. The resulting powder can be redispersed at any convenient time into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals. Methods contemplated for obtaining this powder include freeze-drying, spray drying, and the like.

In accordance with a specific embodiment of the present invention, there is provided a method for the formation of unusually small submicron solid particles containing substantially water insoluble pharmaceutical substance and an Ostwald ripening inhibitor for Ostwald growth, i.e., particles which are less than 200 nanometers in diameter. Such particles are capable of being sterile-filtered before use in the form of a liquid suspension. The ability to sterile-filter the end product of the invention formulation process (i.e., the substantially water insoluble pharmaceutical substance particles) is of great importance since it is impossible to sterilize dispersions which contain high concentrations of protein (e.g., serum albumin) by conventional means such as autoclaving.

In order to obtain sterile-filterable solid nanoparticles of substantially water insoluble pharmaceutical substances (i.e., particles <200 nm), the substantially water insoluble pharmaceutical substance and the Ostwald ripening inhibitor(s) are initially dissolved in a substantially water immiscible organic solvent (e.g., a solvent having less than about 5% solubility in water, such as, for example, chloroform) at high concentration, thereby forming an oil phase containing the substantially water insoluble pharmaceutical substance, the Ostwald ripening inhibitor and other agents. Suitable solvents are set forth above. Next, a water miscible organic solvent (e.g., a solvent having greater than about 10% solubility in water, such as, for example, ethanol) is added to the oil phase at a final concentration in the range of about 1%-99% v/v, more preferably in the range of about 5%-25% v/v of the total organic phase. The water miscible organic solvent can be selected from such solvents as ethyl acetate, ethanol, tetrahydrofuran, dioxane, acetonitrile, acetone, dimethyl sulfoxide, dimethyl formamide, methyl pyrrolidinone, and the like. Alternatively, the mixture of water immiscible solvent with the water miscible solvent is prepared first, followed by dissolution of the substantially water insoluble pharmaceutical substance, the Ostwald ripening inhibitor and other agents in the mixture. It is believed that the water miscible solvent in the organic phase act as a lubricant on the interface between the organic and aqueous phases resulting in the formation of fine oil in water emulsion during homogenization.

In the next stage, for the formation of solid nanoparticles of substantially water insoluble pharmaceutical substances with reduced Ostwald growth, human serum albumin or any other suitable stabilizing agent as described above is dissolved in aqueous media. This component acts as an emulsifying agent for the formation of stable nanodroplets. Optionally, a sufficient amount of the first organic solvent (e.g. chloroform) is dissolved in the aqueous phase to bring it close to the saturation concentration. A separate, measured amount of the organic phase (which now contains the substantially water insoluble pharmaceutical substances, the first organic solvent and the second organic solvent) is added to the saturated aqueous phase, so that the phase fraction of the organic phase is between about 0.5%-15% v/v, and more preferably between 1% and 8% v/v. Next, a mixture composed of micro and nanodroplets is formed by homogenization at low shear forces. This can be accomplished in a variety of ways, as can readily be identified by those of skill in the art, employing, for example, a conventional laboratory homogenizer operated in the range of about 2,000 up to about 15,000 rpm. This is followed by homogenization under high pressure (i.e., in the range of about 3,000 up to 30,000 psi). The resulting mixture comprises an aqueous protein solution (e.g., human serum albumin), the substantially water insoluble pharmaceutical substance, Ostwald ripening inhibitor(s), other agents, the first solvent and the second solvent. Finally, solvent is rapidly evaporated under vacuum to yield a colloidal dispersion system (solids of substantially water insoluble pharmaceutical substance, the Ostwald ripening inhibitor and other agents and protein) in the form of extremely small nanoparticles (i.e., particles in the range of about 50 nm-200 nm diameter), and thus can be sterile-filtered. The preferred size range of the particles is between about 50 nm-170 nm, depending on the formulation and operational parameters.

The solid nanoparticles prepared in accordance with the present invention may be further converted into powder form by removal of the water there from, e.g., by lyophilization at a suitable temperature-time profile. The protein (e.g., human serum albumin) itself acts as a cryoprotectant, and the powder is easily reconstituted by addition of water, saline or buffer, without the need to use such conventional cryoprotectants as mannitol, sucrose, trehalose, glycine, and the like. While not required, it is of course understood that conventional cryoprotectants may be added to invention formulations if so desired. The solid nanoparticles containing substantially water insoluble pharmaceutical substance allows for the delivery of high doses of the pharmacologically active agent in relatively small volumes.

According to this embodiment of the present invention, the solid nanoparticles containing substantially water insoluble pharmaceutical substance has a cross-sectional diameter of no greater than about 2 microns. A cross-sectional diameter of less than 1 microns is more preferred, while a cross-sectional diameter of less than 0.22 micron is presently the most preferred for the intravenous route of administration.

Proteins contemplated for use as stabilizing agents in accordance with the present invention include albumins (which contain 35 cysteine residues), immunoglobulins, caseins, insulins (which contain 6 cysteines), hemoglobins (which contain 6 cysteine residues per $\alpha 2$ $\beta 2$ unit), lysozymes (which contain 8 cysteine residues), immunoglobulins, $\alpha$-2-macroglobulin, fibronectins, vitronectins, fibrinogens, lipases, and the like. Proteins, peptides, enzymes, antibodies and combinations thereof, are general classes of stabilizers contemplated for use in the present invention.

A presently preferred protein for use is albumin Human serum albumin (HSA) is the most abundant plasma protein (~640 μM) and is non-immunogenic to humans. The protein is principally characterized by its remarkable ability to bind a broad range of hydrophobic small molecule ligands including fatty acids, bilirubin, thyroxine, bile acids and steroids; it serves as a solubilizer and transporter for these compounds and, in some cases, provides important buffering of the free concentration. HSA also binds a wide variety of drugs in two primary sites which overlap with the binding locations of endogenous ligands. The protein is a helical monomer of 66 kD containing three homologous domains (I-III) each of which is composed of A and B subdomains. The measurements on erythrosin-bovine serum albumin complex in neutral solution, using the phosphorescence depolarization techniques, are consistent with the absence of independent motions of large protein segments in solution of BSA, in the time range from nanoseconds to fractions of milliseconds. These measurements support a heart shaped structure (8 nm×8 nm×8 nm×3.2 nm) of albumin in neutral solution of BSA as in the crystal structure of human serum albumin (Ferrer 2001). Another advantage of albumin is its ability to transport drugs into tumor sites. Specific antibodies may also be utilized to target the nanoparticles to specific locations.

In the preparation of the inventive compositions, a wide variety of organic media can be employed to suspend or dissolve the substantially water insoluble substantially water insoluble pharmaceutical substances. Organic media contemplated for use in the practice of the present invention include any nonaqueous liquid that is capable of suspending or dissolving the pharmacologically active agent, but does not chemically react with either the polymer employed as emulsifier, or the pharmacologically active agent itself. Examples include vegetable oils (e.g., soybean oil, olive oil, and the like), coconut oil, safflower oil, cotton seed oil, sesame oil, orange oil, limonene oil, aliphatic, cycloaliphatic, or aromatic hydrocarbons having 4-30 carbon atoms (e.g., n-dodecane, n-decane, n-hexane, cyclohexane, toluene, benzene, and the like), aliphatic or aromatic alcohols having 2-30 carbon atoms (e.g., octanol, and the like), aliphatic or aromatic esters having 2-30 carbon atoms (e.g., ethyl caprylate (octanoate), and the like), alkyl, aryl, or cyclic ethers having 2-30 carbon atoms (e.g., diethyl ether, tetrahydrofuran, and the like), alkyl or aryl halides having 1-30 carbon atoms (and optionally more than one halogen substituent, e.g., $CH_3Cl$, $CH_2Cl_2$, $CH_2Cl$—$CH_2Cl$, and the like), ketones having 3-30 carbon atoms (e.g., acetone, methyl ethyl ketone, and the like), polyalkylene glycols (e.g., polyethylene glycol, and the like), or combinations of any two or more thereof.

Especially preferred combinations of organic media contemplated for use in the practice of the present invention typically have a boiling point of no greater than about 200° C., and include volatile liquids such as dichloromethane, chloroform, ethyl acetate, benzene, and the like (i.e., solvents that have a high degree of solubility for the pharmacologically active agent, and are soluble in the other organic medium employed), along with a higher molecular weight (less volatile) organic medium. When added to the other organic medium, these volatile additives help to drive the solubility of the pharmacologically active agent into the organic medium. This is desirable since this step is usually time consuming Following dissolution, the volatile component may be removed by evaporation (optionally under vacuum).

The solid nanoparticle formulations prepared in accordance with the present invention may further contain certain amount of biocompatible surfactants to further stabilize the emulsion during the homogenization in order to reduce the droplet sizes. These biocompatible surfactants can be selected from natural lecithins such as egg lecithin, soy lecithin; plant monogalactosyl diglyceride (hydrogenated) or plant digalactosyl diglyceride (hydrogenated); synthetic lecithins such as dihexanoyl-L-□-lecithin, dioctanoyl-L-□-lecithin, didecanoyl-L-□-lecithin, didodecanoyl-L-□-lecithin, ditetradecanoyl-L-□-lecithin, dihexadecanoyl-L-□-lecithin, dioctadecanoyl-L-□-lecithin, dioleoyl-L-□-lecithin, dilinoleoyl-L-□-lecithin, □-palmito, □-oleoyl-L-□-lecithin, L-□-glycerophosphoryl choline; polyoxyethylated hydrocarbons or vegetable oils such as Cremaphor® EL or RH40, Emulphor® EL-620P or EL-719, Arlacel®-186, Pluronic® F-68; sorbitan esters such as sorbitan monolaurate, sorbitan monostearate, sorbitan monopalmitate, sorbitan tristearate, sorbitan monooleate; PEG fatty acid esters such as PEG 200 dicocoate, PEG 300 distearate, PEG 400 sesquioleate, PEG 400 dioleate; ethoxylated glycerine esters such as POE(20) glycerol monostearate, POE(20) glycerol monooleate; ethoxylated fatty amines such as POE(15) cocorylamine, POE(25) cocorylamine, POE(80) oleylamine; ethoxylated sorbitan esters such as POE(20) sorbitan Monolaurate, POE(20) sorbitan monostearate, POE(20) sorbitan tristearate, POE(20) sorbitan trioleate; ethoxylated fatty acids such as POE(5) oleic acid, POE(5) coconut fatty acid, POE(14) coconut fatty acid, POE(9) stearic acid, POE(40) stearic acid; alcohol-fatty acid esters such as 2-ethylhexyl palmitate, isobutyl oleate, di-tridecyl adipate; ethoxylated alcohols such as POE(2)-2-ethyl hexyl alcohol, POE(10) cetyl alcohol, POE(4) decyl alcohol, POE(6) lauryl alcohol; alkoxylated castor oils such as POE(5) castor oil, POE(25) castor oil, POE(25) hydrogenated castor oil; glycerine esters such as glycerol monostearate, glycerol tri caprylate; polyethylene glycols such as polyethylene glycol-200, polyethylene glycol-300, polyethylene glycol-400; sugar esters such as sucrose fatty acid esters. The percentage of the biocompatible surfactants in the formulation can vary from 0.002% to 1% by weight.

The solid nanoparticle formulations prepared in accordance with the present invention may further contain certain chelating agents. The biocompatible chelating agent to be added to the formulation can be selected from ethylenediaminetetraacetic acid (EDTA), diethylenetriaminepentaacetic acid (DTPA), ethylene glycol-bis(□-aminoethyl ether)-tetraacetic acid (EGTA), N-(hydroxyethyl)-ethylenediaminetriacetic acid (HEDTA), nitrilotriacetic acid (NTA), triethanolamine, 8-hydroxyquinoline, citric acid, tartaric acid, phosphoric acid, gluconic acid, saccharic acid, thiodipropionic acid, acetonic dicarboxylic acid, di(hydroxyethyl) glycine, phenylalanine, tryptophan, glycerin, sorbitol, diglyme and pharmaceutically acceptable salts thereof.

The nanoparticle formulations prepared in accordance with the present invention may further contain certain antioxidants which can be selected from ascorbic acid derivatives such as ascorbic acid, erythorbic acid, sodium ascorbate; thiol derivatives such as thioglycerol, cysteine, acetylcysteine, cystine, dithioerythreitol, dithiothreitol, glutathione; tocopherols; butylated hydroxyanisole; butylated hydroxytoluene; sulfurous acid salts such as sodium sulfate, sodium bisulfite, acetone sodium bisulfite, sodium metabisulfite, sodium sulfite, sodium formaldehyde.

The nanoparticle formulations prepared in accordance with the present invention may further contain certain preservatives if desired. The preservative for adding into the present inventive formulation can be selected from phenol, chlorobutanol, benzylalcohol, methylparaben, propylparaben, benzalkonium chloride and cetylpyridinium chloride.

The solid nanoparticles containing substantially water insoluble pharmaceutical substance and the Ostwald ripening inhibitor with protein, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

For increasing the long-term storage stability, the solid nanoparticle formulations may be frozen and lyophilized in the presence of one or more protective agents such as sucrose, mannitol, trehalose or the like. Upon rehydration of the lyophilized solid nanoparticle formulations, the suspension retains essentially all the substantially water insoluble pharmaceutical substance previously loaded and the particle size. The rehydration is accomplished by simply adding purified or sterile water or 0.9% sodium chloride injection or 5% dextrose solution followed by gentle swirling of the suspension. The potency of the substantially water insoluble pharmaceutical substance in a solid nanoparticle formulation is not lost after lyophilization and reconstitution.

The solid nanoparticle formulation of the present invention is shown to be less prone to Ostwald ripening due to the presence of the Ostwald ripening inhibitors and and are more stable in solution than the formulations disclosed in the prior art. In the present invention, efficacy of solid nanoparticle formulations of the present invention with varying Ostwald ripening inhibitor compositions, particle size, and substantially water insoluble pharmaceutical substance to protein ratio have been investigated on various systems such as human cell lines and animal models for cell proliferative activities.

The solid nanoparticle formulation of the present invention is shown to be less toxic than the substantially water insoluble pharmaceutical substance administered in its free form. Furthermore, effects of the solid nanoparticle formulations and various substantially water insoluble pharmaceutical substances in their free form on the body weight of mice with different sarcomas and healthy mice without tumor have been investigated.

The examples provided here are not intended, however, to limit or restrict the scope of the present invention in any way and should not be construed as providing conditions, parameters, reagents, or starting materials which must be utilized exclusively in order to practice the art of the present invention.

Example 1

Preparation of Unstable Solid Nanoparticle with Cholesterol as Inhibitor

A mixture of 96 mg of cholesterol and 100 mg of docetaxel (Guiyuanchempharm, China) were dissolved in 2.5 mL of chloroform and 0.5 mL of ethanol mixture. A 3% human albumin solution was prepared by dissolving 1.5 gms of human albumin (Sigma-Aldrich Co, USA) in 50 mL of sterile Type I water. The pH of the human albumin solution was adjusted to 6.0-6.8 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany) The resulting emulsion was subjected to high-pressure homogenization (Avestin Inc, USA). The pressure was varied between 15,000 and 20,000 psi and the emulsification process was continued for 5-8 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-4 mm Hg and the bath temperature during evaporation was set at 35° C.

The particle size of the suspension was determined by photon correlation spectroscopy with a Malvern Zetasizer. 2.5 gms of the cryoprotectant trehalose dihydrate (Sigma-Aldrich Co, USA) was dissolved in 10 mL of sterile Type I water and the solution was added to the suspension so that the concentration of trehalose dihydrate in the suspension was in the range of 4-9% by weight. The suspension was sterile-filtered through a 0.22 µm filter (Nalgene, USA). The particle size of the suspension was between 30 and 220 nm. The suspension was frozen below −40° C. and lyophilized. The lyophilized cake was reconstituted prior to further use. One aliquot of the reconstituted solution was stored at 25° C. and the other was stored at 2-6° C. The particle size of the two aliquots were monitored at 24° C. and over a period of eight hours. The particles in both the samples begin to change after 1-2 hours and started precipitating after 4 hours due to Ostwald ripening (FIG. 6). The formulation containing the above composition was designated as unstable due to Ostwald ripening.

Example 2

Preparation of Stable Solid Nanoparticle with Cholesterol and Cholesteryl Stearate as Inhibitors A mixture of 100 mg of cholesterol (Northern Lipids, Canada), 500 mg of cholesteryl stearate (Sigma Aldrich, Mo) and 100 mg of docetaxel (Guiyuanchempharm, China) were dissolved in 2.5 mL of chloroform and 0.5 mL of ethanol mixture. A 5% human albumin solution was prepared by dissolving 2.5 gms of human albumin (Sigma-Aldrich Co, USA) in 50 mL of sterile Type I water. The pH of the human albumin solution was adjusted to 6.0-6.8 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany) The resulting emulsion was subjected to high-pressure homogenization (Avestin Inc, USA). The pressure was varied between 15,000 and 20,000 psi and the emulsification process was continued for 5-8 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-4 mm Hg and the bath temperature during evaporation was set at 35° C.

The particle size of the suspension was determined by photon correlation spectroscopy with a Malvern Zetasizer. 2.5 gms of the cryoprotectant trehalose dihydrate (Sigma-Aldrich Co, USA) was dissolved in 10 mL of sterile Type I water and the solution was added to the suspension so that the concentration of trehalose dihydrate in the suspension was in the range of 4-9% by weight. The suspension was sterile-filtered through a 0.22 µm filter (Nalgene, USA). The particle size of the suspension was between 30 and 220 nm. The suspension was frozen below −40° C. and lyophilized. The lyophilized cake was reconstituted prior to further use. One aliquote of the reconstituted solution was stored at 25° C. and the other was stored at 2-6° C. The particle size of the two aliquots were monitored at 24° C. over a period of 8 days (FIG. 7). The particles size did not change after 48 hours and were stable for four days. The formulation containing the above composition was designated as stable due to Ostwald ripening.

Example 3

Preparation of Stable Solid Nanoparticle with Cholesterol and Cholesteryl Stearate as Inhibitors A mixture of 50 mg of cholesterol (Northern Lipids, Canada), 250 mg of cholesteryl stearate (Sigma Aldrich, Mo) and 100 mg of docetaxel (Guiyuanchempharm, China) were dissolved in 2.5 mL of chloroform and 0.5 mL of ethanol mixture. A 5% human albumin solution was prepared by dissolving 2.5 gms of human albumin (Sigma-Aldrich Co, USA) in 50 mL of sterile Type I water. The pH of the human albumin solution was adjusted to 6.0-6.8 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany) The resulting emulsion was subjected to high-pressure homogenization (Avestin Inc, USA). The pressure was varied between 15,000 and 20,000 psi and the emulsification process was continued for 5-8 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-2 mm Hg and the bath temperature during evaporation was set at 35° C.

The particle size of the suspension was determined by photon correlation spectroscopy with a Malvern Zetasizer. 2.5 gms of the cryoprotectant trehalose dihydrate (Sigma-Aldrich Co, USA) was dissolved in 10 mL of sterile Type I water and the solution was added to the suspension so that the concentration of trehalose dihydrate in the suspension was in the range of 4-9% by weight. The suspension was sterile-filtered through a 0.22 µm filter (Nalgene, USA). The particle size of the suspension was between 30 and 220 nm. The suspension was frozen below −40° C. and lyophilized. The lyophilized cake was reconstituted prior to further use One aliquote of the reconstituted solution was stored at 25° C. and the other was stored at 2-6° C. The particle size of the two aliquots were monitored at 24° C. over a period of 8 days. The particles size did not change after 48 hours and were stable for 3 days. The formulation containing the above composition was designated as stable due to Ostwald ripening.

Example 4

Preparation of Stable Solid Nanoparticle with Cholesterol and Hexadecyl Hexadecanoate as Inhibitors A mixture of 100 mg of cholesterol (Northern Lipids, Canada), 500 mg of hexadecyl hexadecanoate (Sigma Aldrich, Mo) and 100 mg of docetaxel (Guiyuanchempharm, China) were dissolved in 2.0 mL of chloroform and 0.5 mL of ethanol mixture. A 5% human albumin solution was prepared by dissolving 2.5 gms of human albumin (Sigma-Aldrich Co, USA) in 50 mL of sterile Type I water. The pH of the human albumin solution was adjusted to 6.0-6.8 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany) The resulting emulsion was subjected to high-pressure homogenization (Avestin Inc, USA). The pressure was varied between 15,000 and 20,000 psi and the emulsification process was continued for 5-8 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-2 mm Hg and the bath temperature during evaporation was set at 35° C.

The particle size of the suspension was determined by photon correlation spectroscopy with a Malvern Zetasizer. 2.5 gms of the cryoprotectant trehalose dihydrate (Sigma-Aldrich Co, USA) was dissolved in 10 mL of sterile Type I water and the solution was added to the suspension so that the concentration of trehalose dihydrate in the suspension was in the range of 4-9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. One aliquote of the reconstituted solution was stored at 25° C. and the other was stored at 2-6° C. The particle size of the two aliquots were monitored at 24° C. over a period of 8 days (FIG. 8). The particles size did not change after 48 hours and were stable for five days. The formulation containing the above composition was designated as stable due to Ostwald ripening.

Example 5

Preparation of Stable Solid Nanoparticle with Cholesterol and Glyceryl Tristearate as Inhibitors A mixture of 100 mg of cholesterol (Northern Lipids, Canada), 200 mg of glyceryl tristearate (Sigma Aldrich, Mo) and 100 mg of docetaxel (Guiyuanchempharm, China) were dissolved in 3.0 mL of chloroform and 0.5 mL of ethanol mixture. A 5% human albumin solution was prepared by dissolving 2.5 gms of human albumin (Sigma-Aldrich Co, USA) in 50 mL of sterile Type I water. The pH of the human albumin solution was adjusted to 6.0-6.8 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany) The resulting emulsion was subjected to high-pressure homogenization (Avestin Inc, USA). The pressure was varied between 15,000 and 20,000 psi and the emulsification process was continued for 5-8 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-2 mm Hg and the bath temperature during evaporation was set at 35° C.

The particle size of the suspension was determined by photon correlation spectroscopy with a Malvern Zetasizer. 2.5 gms of the cryoprotectant trehalose dihydrate (Sigma-Aldrich Co, USA) was dissolved in 10 mL of sterile Type I water and the solution was added to the suspension so that the concentration of trehalose dihydrate in the suspension was in the range of 4-9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. One aliquote of the reconstituted solution was stored at 25° C. and the other was stored at 2-6° C. The particle size of the two aliquots was monitored at 24° C. over a period of 8 days (FIG. 9). The particles size did not change after 48 hours and were stable for five days. The formulation containing the above composition was designated as stable due to Ostwald ripening.

Example 6

Effect of Emulsification on Human Serum Albumin

An organic phase was prepared by mixing 3.5 mL of chloroform and 0.6 mL of dehydrated ethanol. A 4% human albumin solution was prepared by dissolving 2 gm of human albumin (Sigma-Aldrich Co, USA) in 50 mL of sterile Type I water. The pH of the human albumin solution was adjusted to 6.0-6.7 by adding either 1N hydrochloric acid or 1N sodium hydroxide solution in sterile water. The above organic solution was added to the albumin phase and the mixture was pre-homogenized with a IKA homogenizer at 6000-10000 RPM (IKA Works, Germany). The resulting emulsion was subjected to high-pressure homogenization (Avestin Inc, USA). The pressure was varied between 20,000 and 30,000 psi and the emulsification process was continued for 5-8 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to obtain an albumin solution subjected to high pressure homogenization. The evaporator pressure was set during the evaporation by a vacuum pump (Welch) at 1-5 mm Hg and the bath temperature during evaporation was set at 35° C.

The particle size of the albumin solution was determined by photon correlation spectroscopy with a Malvern Zetasizer. It was observed that there were two peaks, one around 5-8 nm and other around 120-140 nm. The peak around 5-8 nm contained nearly 99% by volume and the peak around 120-140 nm had less than 1% by volume (FIG. 4). As a control, the particle size distribution in 4% human serum solution was measured. It had only one peak around 5-8 nm (FIG. 5). These studies show that the homogenization of an albumin solution in an oil-in-water emulsion renders less than 2-3 percent of the albumin molecules to be aggregated by denaturation.

Example 7

Preparation of Unstable Solid Nanoparticles without any Inhibitor 100 mg of docetaxel (Guiyuanchempharm, China) was dissolved in 2.5 mL of chloroform and 0.5 mL of ethanol mixture. A 5% bovine serum albumin solution was prepared by dissolving 2.5 gms of bovine serum albumin (Sigma-Aldrich Co, USA) in 50 mL of sterile Type I water. The pH of the human albumin solution was adjusted to 6.0-6.8 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany). The resulting emulsion was subjected to high-pressure homogenization (Avestin Inc, USA). The pressure was varied between 15,000 and 20,000 psi and the emulsification process was continued for 8-12 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-3 mm Hg and the bath temperature during evaporation was set at 35° C.

It was noticed that after evaporation, the solution was more turbid than other formulations. 2.5 gms of the cryoprotectant trehalose dihydrate (Sigma-Aldrich Co, USA) was dissolved in 10 mL of sterile Type I water and the solution was added to the suspension so that the concentration of trehalose dihydrate in the suspension was in the range of 4-9% by weight. The suspension was filtered through a 0.45 μm filter and it required more than 2 70 mm filters to filter the solution. The solution was again filtered through 0.22 μm filter (Nalgene, USA). The filters were washed each with 25 mL of acetonitrile to recover the precipitated drug on the filters. The particle size of the suspension was determined by photon correlation spectroscopy with a Malvern Zetasizer. The particle size of the 0.22 μm filtered suspension was between 240-390 nm (FIG. 10). The docetaxel concentration was determined by HPLC method for the 0.22 μm filtered suspension and the recovered docetaxel from the filters. It was noticed that nearly 50% of docetaxel was recovered from the filters and the remaining was in the suspension. One aliquote of the suspension was stored at 25° C. and the other was stored at 2-6° C. The particles in both the samples began to change after 1-3 hours and started precipitating after 8 hours due to Ostwald ripening.

The formulation was prepared again and observed the same precipitation problem as above. The formulation containing the above composition was designated as unstable due to Ostwald ripening.

Example 8

Preparation of Unstable Solid Nanoparticle without any Inhibitor 160 mg of docetaxel (Guiyuanchempharm, China) was dissolved in 2.5 mL of chloroform and 0.5 mL of ethanol mixture. A 5% human serum albumin solution was prepared by dissolving 2.5 gms of human serum albumin (Sigma-Aldrich Co, USA) in 50 mL of sterile Type I water. The pH of the albumin solution was adjusted to 6.2-6.5 by adding either 1N hydrochloric acid or 1N sodium hydroxide solution in sterile water. The above organic solution was added to the albumin phase and the mixture was pre-homogenized with a IKA homogenizer at 4000-6000 RPM (IKA Works, Germany). The resulting emulsion was subjected to high-pressure homogenization (Avestin Inc, USA). The pressure was varied between 15,000 and 24,000 psi and the emulsification process was continued for 8-12 passes. During homogenization the emulsion was cooled between 5° C. and 10° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a vacuum pump (Welch) at 0.5-3 mm Hg and the bath temperature during evaporation was set at 35° C.

It was noticed that after evaporation, the solution was more turbid than other formulations. The particle size of the suspension was determined by photon correlation spectroscopy with a Malvern Zetasizer. The particle size of the unfiltered suspension was between 200-1000 nm (FIG. 11). One aliquote of the suspension was stored at 20-25° C. and the other was stored at 2-6° C. The particles in both the samples began to change after 1-3 hours and started precipitating after 8 hours due to Ostwald ripening. The formulation containing the above composition was designated as unstable due to Ostwald ripening.

INDUSTRIAL APPLICABILITY

This invention can be used for any purpose that is related to the creation of substantially stable dispersions of solid particles of a non-water soluble substance in an aqueous medium, prepared using an oil-in-water emulsion process using protein or other polymer as a surfactant and the dispersions prepared according to the present invention exhibit little or no particle growth after the formation mediated by Ostwald ripening. The invention can be used to create water soluble compositions for use as a cancer treatment, but persons skilled in the art will see other applications as well.

What is claimed is:
1. A process for the preparation of a substantially stable dispersion of solid nano-particles with a mean size of less than 240 nm in an aqueous medium, the process comprising: combining
    (a) an aqueous phase comprising water and an emulsifier; with

(b) an organic phase comprising a substantially water-insoluble substance, a water-immiscible organic solvent, optionally a water-miscible organic solvent as an interfacial lubricant, and an Ostwald ripening inhibitor;

(c) forming an oil-in-water emulsion using a high pressure homogenizer;

(d) removing the water-immiscible organic solvent, and the optional organic solvent used as an interfacial lubricant, from the medium under vacuum; thereby forming solid particles comprising the inhibitor and the substantially water-insoluble substance; and optionally wherein:

(i) the Ostwald ripening inhibitor is a non-polymeric hydrophobic organic compound that is substantially insoluble in water;

(ii) the Ostwald ripening inhibitor is less soluble in water than the substantially water-insoluble substance; and (iii) the Ostwald ripening inhibitor is not a phospholipid;

wherein the Ostwald ripening inhibitor is selected from the group consisting of 1) a mixture of cholesteryl esters obtainable by esterifying cholesterol with a mixture of medium and large chain fatty acids;
2) cholesterol; and
3) cholesterol and a mixture of cholesteryl esters obtainable by esterifying cholesterol with a mixture of medium and large chain fatty acids.

2. The process according to claim 1, wherein the emulsifier is a protein and said protein is selected from albumins, immunoglobulins, caseins, insulins, hemoglobins, lysozymes, α-2-macroglobulin, fibronectins, vitronectins, fibrinogens, lipases, enzymes and antibodies.

3. The process according to claim 2 wherein said protein is human serum albumin.

4. A substantially stable aqueous dispersion prepared according to claim 1 wherein the dispersion comprises a continuous aqueous phase and solid particles dispersed in the continuous aqueous phase, wherein the solid particles comprise an Ostwald ripening inhibitor and a substantially water-insoluble substance and wherein:

(i) the Ostwald ripening inhibitor is a non-polymeric hydrophobic organic compound that is substantially insoluble in water;

(ii) the Ostwald ripening inhibitor is less soluble in water than the substantially water-insoluble substance; and (iii) the Ostwald ripening inhibitor is not a phospholipid;

wherein the Ostwald ripening inhibitor is selected from the group consisting of 1) a mixture of cholesteryl esters obtainable by esterifying cholesterol with a mixture of medium and large chain fatty acids;
2) cholesterol; and
3) cholesterol and a mixture of cholesteryl esters obtainable by esterifying cholesterol with a mixture of medium and large chain fatty acids.

5. A pharmaceutical formulation comprising the substantially stable dispersion of solid nano-particles according to claim 1 in association with a pharmaceutically acceptable carrier or diluent.

6. A method for inhibiting Ostwald ripening in a dispersion of solid nano-particles of a substantially water-insoluble substance in an aqueous medium, the method comprising: combining (a) an aqueous phase comprising water and an emulsifier; with (b) an organic phase comprising a substantially water-insoluble substance, a water-immiscible organic solvents, optionally a water-miscible organic solvent as an interfacial lubricant and an Ostwald ripening inhibitor;

(c) forming an oil-in-water emulsion using a high pressure homogenizer;

(d) removing the water-immiscible organic solvent, and the optional water-miscible organic solvent used as an interfacial lubricant, from the dispersion under vacuum; thereby forming solid particles comprising the Ostwald ripening inhibitor and the substantially water-insoluble substance to give a dispersion of the solid substantially water-insoluble particles in an aqueous medium; wherein:

(i) the Ostwald ripening inhibitor is a non-polymeric hydrophobic organic compound that is substantially insoluble in water;

(ii) the Ostwald ripening inhibitor is less soluble in water than the substantially water-insoluble substance; and (iii) the Ostwald ripening inhibitor is not a phospholipid;

wherein the Ostwald ripening inhibitor is selected from the group consisting of 1) a mixture of cholesteryl esters obtainable by esterifying cholesterol with a mixture of medium and large chain fatty acids;
2) cholesterol; and
3) cholesterol and a mixture of cholesteryl esters obtainable by esterifying cholesterol with a mixture of medium and large chain fatty acids.

7. The method according to claim 6, wherein the mean particle size of the solid particles is less than 1 μm.

8. A nanoparticle composition containing a substantially water insoluble pharmaceutical substance produced by the method of claim 1 further comprising pharmaceutically acceptable preservative(s).

9. A solid nanoparticle lipid composition comprising a substantially water insoluble pharmaceutical substance produced by the process of claim 1, further comprising biocompatible excipients.

10. The process of claim 1, wherein the Ostwald ripening inhibitor is a mixture of cholesteryl esters obtainable by esterifying cholesterol with a mixture of medium and large chain fatty acids.

11. The process of claim 1, wherein the Ostwald ripening inhibitor is cholesterol.

12. The process of claim 1, wherein the Ostwald ripening inhibitor is cholesterol and a mixture of cholesteryl esters obtainable by esterifying cholesterol with a mixture of medium and large chain fatty acids.

* * * * *